(12) United States Patent
Sinha et al.

(10) Patent No.: US 9,187,420 B2
(45) Date of Patent: Nov. 17, 2015

(54) PYRROLE DERIVATIVES AS NICOTINIC ACETYLCHOLINE RECEPTOR MODULATORS FOR USE IN THE TREATMENT OF NEURODEGENERATIVE DISORDERS SUCH AS ALZHEIMER'S AND PARKINSON'S DISEASE

(75) Inventors: Neelima Sinha, Pune (IN); Gourhari Jana, Pune (IN); Ajay Ramchandra Tilekar, Pune (IN); Navnath Popat Karche, Pune (IN); Venkata P. Palle, Pune (IN); Rajender Kumar Kamboj, Pune (IN)

(73) Assignee: Lupin Limited, Mumbai (IN)

( * ) Notice: Subject to any disclaimer, the term of this patent is extended or adjusted under 35 U.S.C. 154(b) by 0 days.

(21) Appl. No.: 14/007,458

(22) PCT Filed: Mar. 27, 2012

(86) PCT No.: PCT/IB2012/051451
§ 371 (c)(1),
(2), (4) Date: Sep. 25, 2013

(87) PCT Pub. No.: WO2012/131576
PCT Pub. Date: Oct. 4, 2012

(65) Prior Publication Data
US 2014/0018327 A1 Jan. 16, 2014

(30) Foreign Application Priority Data
Mar. 31, 2011 (IN) .............................. 458/KOL/2011

(51) Int. Cl.
| | |
|---|---|
| C07D 207/333 | (2006.01) |
| C07D 207/34 | (2006.01) |
| A61K 31/402 | (2006.01) |
| A61K 45/06 | (2006.01) |
| A61K 31/635 | (2006.01) |
| C07D 207/335 | (2006.01) |

(52) U.S. Cl.
CPC ............ *C07D 207/34* (2013.01); *A61K 31/402* (2013.01); *A61K 31/635* (2013.01); *A61K 45/06* (2013.01); *C07D 207/333* (2013.01); *C07D 207/335* (2013.01)

(58) Field of Classification Search
CPC .................................................. C07D 207/333
See application file for complete search history.

(56) References Cited

U.S. PATENT DOCUMENTS

| | | | |
|---|---|---|---|
| 4,235,871 A | 11/1980 | Papahadjopoulos et al. | |
| 4,501,728 A | 2/1985 | Geho et al. | |
| 4,837,028 A | 6/1989 | Allen | |
| 5,019,369 A | 5/1991 | Presant et al. | |
| 7,683,084 B2 | 3/2010 | Faghih et al. | |
| 7,741,364 B2 | 6/2010 | Faghih et al. | |
| 2006/0142349 A1 | 6/2006 | Hurst et al. | |
| 2007/0142450 A1 | 6/2007 | Dahl et al. | |
| 2009/0253691 A1 | 10/2009 | Thuring et al. | |
| 2010/0190819 A1 | 7/2010 | Kanner | |
| 2010/0216748 A1 * | 8/2010 | Faghih et al. | 514/151 |
| 2010/0222398 A1 | 9/2010 | Nardi et al. | |
| 2010/0227869 A1 | 9/2010 | Peters et al. | |
| 2010/0240707 A1 | 9/2010 | Thuring et al. | |

FOREIGN PATENT DOCUMENTS

| | | |
|---|---|---|
| EP | 2168959 A1 | 3/2010 |
| EP | 1866314 B1 | 9/2010 |
| WO | 2004029066 A2 | 4/2004 |
| WO | 2007031440 A2 | 3/2007 |
| WO | 2009043780 A1 | 4/2009 |
| WO | 2009043784 A1 | 4/2009 |
| WO | 2009115547 A1 | 9/2009 |
| WO | 2009127678 A1 | 10/2009 |

(Continued)

OTHER PUBLICATIONS

Micheli et al. (Bioorg. Med. Chem. 11 (2003) 171-183).*

(Continued)

*Primary Examiner* — Robert Havlin
(74) *Attorney, Agent, or Firm* — The Webb Law Firm

(57) ABSTRACT

Disclosed is a compound of formula (I) wherein 'a' and $R^1$-$R^5$ are as described herein, as a modulator of nicotinic acetylcholine receptors particularly the α7 subtype, in a subject in need thereof, as well as analogs, prodrugs, isotopically substituted analogs, metabolites, pharmaceutically acceptable salts, polymorphs, solvates, isomers, clathrates, and co-crystal thereofs, for use either alone or in combinations with suitable other medicaments, and pharmaceutical compositions containing such compounds and analogs. Also disclosed are a process of preparation of the compounds and the intended uses thereof in therapy, particularly in the prophylaxis and therapy of disorders such as Alzheimer's disease, mild cognitive impairment, senile dementia, and the like.

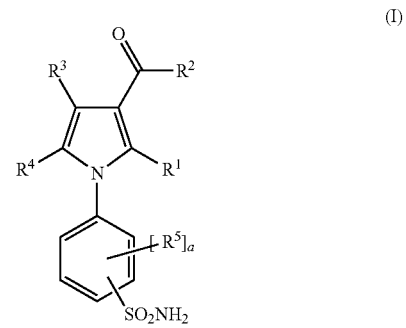

7 Claims, No Drawings

(56) References Cited

FOREIGN PATENT DOCUMENTS

| WO | 2009127679 A1 | 10/2009 |
| WO | 2009135944 A1 | 11/2009 |
| WO | 2009145996 A2 | 12/2009 |
| WO | 2010130768 A1 | 11/2010 |
| WO | 2011036167 A1 | 3/2011 |
| WO | 2011064288 A1 | 6/2011 |

OTHER PUBLICATIONS

Kubinyi (3D QSAR in Drug Design: Ligand-Protein Interactions and Molecular Similarity, vol. 2-3, Springer, 1998, 800 pages). pp. 243-244 provided.*
Wermuth, The Practice of Medicinal Chemsitry, 2d ed. (2003), 768 pages. Chs. 9-10 provided.*
Ng HJ et al., Proc. Natl. Acad. Sci., U. S. A, 2007, 104, 8059-8064.
Nizri E et al., Drug News Perspect., 2007, 20, 421-429.
Nordberg A et al., Neurotox. Res., 2000, 2, 157-165.
O'Donnell CJ et al., J. Med. Chem., 2010, 53, 1222-1237.
Olincy A et al., Arch. Gen. Psychiatry, 2006, 63, 630-638.
Olincy A et al., Biol. Psychiatry, 2005, 57(8, Suppl.), Abst 44.
Paterson D et al., Prog. Neurobiol., 2000, 61, 75-111.
Pena G et al., Eur. J. Immunol., 2010,40, 2580-2589.
Peng ZZ et al., Zhonghua Yi Xue Yi Chuan Xue Za Zhi, 2008, 25, 154-158 (English-Language Abstract Attached).
Perry E et al., Eur. J. Pharmacol., 2000, 393, 215-222.
Physicians' Desk Reference, 58th ed., Thomson PDR (2004).
Pichat P et al., Neuropsychopharmacology, 2007, 32, 17-34.
Redrobe JP et al., Eur. J. Pharmacol., 2009, 602, 58-65.
Remington's Pharmaceutical Science, 17th ed., Mack Publishing Company, Easton, PA, 1985.
Remington's Pharmaceutical Sciences, 18th ed., Mack Publishing Company, Easton, PA, 1990, p. 1445.
Roncarati R et al., J. Pharmacol. Exp. Ther., 2009, 329, 459-468.
Rosas-Ballina M et al., Mol. Med., 2009, 15, 195-202.
Rosas-Ballina M et al., J. Intern. Med., 2009, 265, 663-679.
Rowbotham MC et al., Pain, 2009, 146, 245-252.
Rowley TJ et al., Br. J. Anaesth., 2010, 105, 201-207.
Rubboli F et al., Neurochem. Int., 1994, 25, 69-71.
Sanberg PR et al., Pharmacol. Ther., 1997, 74, 21-25.
Schuller HM et al., Eur. J. Pharmacol., 2000, 393, 265-277.
Solinas M et al., J. Neurosci., 2007, 27, 5615-5620.
Suemaru K et al., Nippon Yakurigaku Zasshi, 2002, 119, 295-300 (English-Language Abstract Attached).
Syn. Lett. 2005, 13, 2089-2091.
Szoka et al., Ann. Rev. Biophys. Bioeng., 9, 467 (1980).
Tet. Lett. 2007, 48, 5181-5184.
Thomsen MS et al., Curro Pharm. Des., 2010, 16, 323-343.
Timmermann DB et al., J. Pharmacol. Exp. Ther., 2007, 323, 294-307.
Tsuang DW et al., Am. J. Med. Genet., 2001, 105, 662-668.
Van KM et al., Psychopharmacology (Berl) 2004, 172, 375-383.
Verbois SL et al., Neuropharmacology, 2003, 44, 224-233.
Nagele RG et al., Neuroscience, 2002, 110, 199-211.
Wang HY et al., J. Neurosci., 2009, 29, 10961-10973.
Wang J et al., J. Neurosci. Res., 2010, 88, 807-815.
Wasserman et al., Cancer, 36, pp. 1258-1268 (1975).
Weiss RB et al., PLoS Genet., 2008, 4, e1000125.
Westman M et al., Scand. J. Immunol., 2009, 70, 136-140.
Wilens TE et al., Biochem. Pharmacol., 2007, 74, 1212-1223.
Young JW et al., Eur. Neuropsychopharmacol., 2007, 17, 145-155.
Young JW et al., Neuropsychopharmacology, 2004, 29, 891-900.
Zhao X et al., Ann. N. Y. Acad. Sci., 2001, 939, 179-186.
Albuquerque EX et al., Alzheimer Dis. Assoc. Disord., 2001, 15 Suppl 1, SI9-S25.
Alkondon M et al., Eur. J. Pharmacol., 2000, 393 59-67.
Arias HR et al., Int. J. Biochem. Cell. Biol., 2009, 41, 1441-1451.
Bennouna M et al., Encephale, 2007, 33, 616-620 (English-Language Abstract Attached).
Berge S.M. et al. Pharmaceutical Salts, a review article in Journal of Pharmaceutical sciences vol. 66, p. 1-19 (1977).
Bitner RS et al., J. Neurosci., 2007, 27, 10578-10587.
Boess FG et al., J. Pharmacol. Exp. Ther., 2007, 321, 716-725.
Bruchfeld A et al., J. Intern. Med., 2010, 268, 94-101.
Calleja-Macias IE et al., Int. J. Cancer., 2009, 124, 1090-1096.
Cannon 1D et al., Curro Opin. Psychiatry, 2005, 18, 135-140.
Carson R et al., Neuromolecular, 2008, Med. 10, 377-384.
Chan WK et al., Neuropharmacology, 2007, 52, 1641-1649.
Chem. Pharm. Bull. 1982, 30, 2590.
Chemistry, A European Journal, 2011, 17(21), 5903-5907.
Curzon P et al., Neurosci. Lett., 2006, 410, 15-19.
Dajas-Bailador F et al., Trends Pharmacol. Sci., 2004, 25, 317-324.
Damaj MI et al., Neuropharmacology, 2000, 39, 2785-2791.
Decker MW et al., Expert. Opin. Investig. Drugs, 2001, 10, 1819-1830.
Deutsch SI et al., Clin. Neuropharmacol., 2003, 26, 277-283.
Donnelly-Roberts DL et al., J. Pharmacol. Exp. Ther., 1998, 285, 777-786.
Dunlop J et al., J. Pharmacol. Exp. Ther., 2009, 328, 766-776.
Duris K et al., Stroke 2011, 42(12), 3530-6.
Ebbed JO et al., Patient. Prefer. Adherence, 2010, 4, 355-362.
EnVivo Pharmaceuticals press release, Jan 12, 2009.
Faghih R et al., J. Med. Chem., 2009, 52, 3377-3384.
Feher A et al., Dement. Geriatr. Cogn. Disord., 2009, 28, 56-62.
Freedman R et al., Curro Psychiatry Rep., 2003, 5, 155-161.
Freedman R et al., Biol. Psychiatry, 1995, 38, 22-33.
Gallowitsch-Puerta M et al., Life Sci., 2007, 80, 2325-2329.
Giebelen IA T et al., Shock, 2007, 27, 443-447.
Goldstein R et al., Acad. Emerg. Med., 2007, 14 (15, Suppl. 1), Abst 474.
Handbook of pharmaceutical salts properties, selection, and use by P. H. Heinrich Stahland Camille G.wermuth, Wiley-VCH (2002).
Harrington CR et al., Dementia, 1994, 5, 215-228.
Hashimoto K et al., Biol. Psychiatry, 2008, 63, 92-97.
Hauser TA et al., Biochem. Pharmacol., 2009, 78, 803-812.
Haydar SN et al., Bioorg. Med. Chem., 2009, 17, 5247-5258.
Heeschen C et al., J. Clin. Invest, 2002, 110, 527-536.
Jeyarasasingam G et al., Neuroscience, 2002, 109, 275-285.
Jin Y et al. (2010) Int. J. Immunogenet., 37, 361.
Liu C et al., Crit. Care. Med., 2009, 37, 634-641.
Journal of Med. Chemistry, 1997, 40, 547.
Kuzmin A et al., Psychopharmacology (Berl), 2009, 203, 99-108.
Leiser SC et al., Pharmacol. Ther., 2009, 122, 302-311.
Leonard S et al., Pharmacol. Biochem. Behav., 2001, 70, 561-570.
Mansvelder HD et al., Psychopharmacology (Berl), 2006, 184, 292-305.
Marrero MB et al., Brain. Res., 2009, 1256, 1-7.
Martin LF et al., Am. J. Med. Genet., B Neuropsychiatr. Genet., 2007, 144B, 611-614.
Martin LF et al., Psychopharmacology (Berl), 2004, 174, 54-64.
McKay BE et al., Biochem. Pharmacol., 2007,74, 1120-1133.
Med. Chem. Res. (1994), 5, 54-62.

* cited by examiner

PYRROLE DERIVATIVES AS NICOTINIC ACETYLCHOLINE RECEPTOR MODULATORS FOR USE IN THE TREATMENT OF NEURODEGENERATIVE DISORDERS SUCH AS ALZHEIMER'S AND PARKINSON'S DISEASE

CROSS-REFERENCE TO RELATED APPLICATIONS

This application is the United States national phase of International Application No. PCT/IB2012/051451 filed Mar. 27, 2012, and claims priority to Indian Patent Application No. 458/KOL/2011 filed Mar. 31, 2011, the disclosures of which are hereby incorporated in their entirety by reference.

FIELD OF THE INVENTION

The present invention is related to novel compounds of the general formula I,

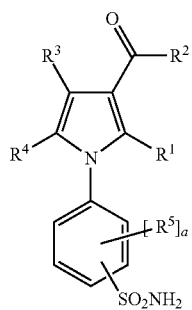

(I)

their tautomeric forms, their stereoisomers, their analogues, their prodrugs, their isotopically labeled analogues, their N-oxides, their metabolites, their pharmaceutically acceptable salts, polymorphs, solvates, optical isomers, clathrates, co-crystals, combinations with suitable medicament, pharmaceutical compositions containing them, methods of making of the above compounds, and their use as nicotinic acetylcholine receptor α7 subunit (α7 nAChR) modulator.

BACKGROUND OF THE INVENTION

Cholinergic neurotransmission, mediated primarily through the neurotransmitter acetylcholine (ACh), is a predominant regulator of the physiological functions of the body via the central and autonomic nervous system. ACh acts on the synapses of the neurons present in of all the autonomic ganglia, neuromuscular junctions and the central nervous system. Two distinct classes of ACh target receptors viz. muscarinic (mAChRs) and the nicotinic (nAChRs) have been identified in brain, forming a significant component of receptors carrying its mnemonic and other vital physiological functions.

Neural nicotinic ACh receptors (NNRs) belong to the class of ligand-gated ion channels (LGIC) comprising of five subunits (α2-α10, β2-β4) arranged in heteropentameric (α4β2) or homopertameric (α7) configuration (Paterson D et al., Prog. Neurobiol., 2000, 61, 75-111). α4β2 and α7 nAChR constitute the predominant subtypes expressed in the mammalian brain. α7 nAChR has attained prominence as a therapeutic target due to its abundant expression in the learning and memory centers of brain, hippocampus and the cerebral cortex (Rubboli F et al., Neurochem. Int., 1994, 25, 69-71). Particularly, α7 nAChR is characterized by a high $Ca^{2+}$ ion permeability, which is responsible for neurotransmitter release and consequent modulation of excitatory and inhibitory neurotransmission (Alkondon M et al., Eur. J. Pharmacol., 2000, 393, 59-67; Dajas-Bailador F et al., Trends Pharmacol. Sci., 2004, 25, 317-324). Furthermore, high $Ca^{2+}$ ion influx also has implications on the long-term potentiation of memory via alterations in gene expression (Bitner R S et al., J. Neurosci., 2007, 27, 10578-10587; McKay B E et al., Biochem. Pharmacol., 2007, 74, 1120-1133).

Several recent studies have confirmed the role of α7 nAChR in neural processes like attention, memory and cognition (Mansvelder H D et al., Psychopharmacology (Berl), 2006, 184, 292-305; Chan W K et al., Neuropharmacology, 2007, 52, 1641-1649; Young J W et al., Eur. Neuropsychopharmacol., 2007, 17, 145-155). Gene polymorphisms associated with the α7 nAChR protein CHRNA7 have been implicated in the genetic transmission of schizophrenia, related neurophysiological sensory gating deficits and resultant cognitive impairment (Freedman R et al., Biol. Psychiatry, 1995, 38, 22-33; Tsuang D W et al., Am. J. Med. Genet., 2001, 105, 662-668). Also, preclinical studies in α7 nAChR knock-out and anti-sense oligonucleotide treated mice have demonstrated impaired attention and defective cognition underscoring the prominent role of α7 nAChR in cognition (Curzon P et al., Neurosci. Lett., 2006, 410, 15-19; Young J W et al., Neuropsychopharmacology., 2004, 29, 891-900). Additionally, pharmacological blockade of α7 nAChR impairs memory and its activation enhances same in preclinical rodent models implicating α7 nAChR as target for cognitive enhancement (Hashimoto K et al., Biol. Psychiatry, 2008, 63, 92-97).

Pathological brain function in sensory-deficit disorders has been associated with nicotinic cholinergic transmission particularly through α7 receptors (Freedman R et al., Biol. Psychiatry, 1995, 38, 22-33; Tsuang D W et al., Am. J. Med. Genet., 2001, 105, 662-668; Carson R et al., Neuromolecular, 2008, Med. 10, 377-384; Leonard S et al., Pharmacol. Biochem. Behav., 2001, 70, 561-570; Freedman R et al., Curr. Psychiatry Rep., 2003, 5, 155-161; Cannon T D et al., Curr. Opin. Psychiatry, 2005, 18, 135-140). A defective pre-attention processing of sensory information is understood to be the basis of cognitive fragmentation in schizophrenia and related neuropsychiatric disorders (Leiser S C et al., Pharmacol. Ther., 2009, 122, 302-311). Genetic linkage studies have traced sharing of the α7 gene locus for several affective, attention, anxiety and psychotic disorders (Leonard S et al., Pharmacol. Biochem. Behav., 2001, 70, 561-570; Suemaru K et al., Nippon Yakurigaku Zasshi, 2002, 119, 295-300).

Perturbations in the cholinergic and glutamatergic homeostasis, has long been implicated as causative factors for host of neurological disease, including dementia(s) (Nizri E et al., Drug News Perspect., 2007, 20, 421-429). Dementia is a severe, progressive, multi-factorial cognitive disorder affecting memory, attention, language and problem solving. Nicotinic ACh receptor, particularly the interaction of α7 receptor to $\alpha\beta_{1-42}$ is implicated as an up-stream pathogenic event in Alzheimer's disease, a major causative factor for dementia (Wang H Y et al., J. Neurosci., 2009, 29, 10961-10973). Moreover, gene polymorphisms in CHRNA7 have been implicated in dementia with lewy bodies (DLB) and Pick's disease (Feher A et al., Dement. Geriatr. Cogn. Disord., 2009, 28, 56-62).

Disease modification potential of nAChRs particularly the α7 receptor has application for disease-modification of Alzheimer's disease (AD) and Parkinson's disease (PD) by enhancing neuron survival and preventing neurodegeneration (Wang et al. 2009; Nagele R G et al., Neuroscience, 2002, 110, 199-211; Jeyarasasingam G et al., Neuroscience, 2002, 109, 275-285). Additionally, α7 nAChR induced activation of anti-apoptotic (BCL-2) and anti-inflammatory pathways in brain could have neuroprotective effects in neurodegenerative diseases (Marrero M B et al., Brain. Res., 2009, 1256, 1-7). Dopamine containing neurons of ventral tegmental area (VTA) and laterodorsal tegmental nucleus (LDT) are known to express nicotinic ACh receptors, particularly α4, α3, β2, β3, β4 subunits (Kuzmin A et al., Psychopharmacology (Berl), 2009, 203, 99-108). Nicotinic ACh receptors, α4β2 and α3β4 have been identified with candidate-gene approach to have strong mechanistic link for nicotine addiction (Weiss R B et al., PLoS Genet., 2008, 4, e1000125). α7 nAChR has particularly been studied for a putative role in cannabis addiction (Solinas M et al., J. Neurosci., 2007, 27, 5615-5620). Varenicline, a partial agonist at α4β2, has demonstrated better efficacy in reducing the smoking addiction and relapse prevention in comparison to buproprion (Ebbert J O et al., Patient. Prefer. Adherence, 2010, 4, 355-362).

Presence of a high-affinity nicotine binding site at α4β2 nAChR, in the descending inhibitory pathways from brainstem has sparked interest in the antinociceptive properties of nicotinic ACh receptor agonists like epibatidine (Decker M W et al., Expert. Opin. Investig. Drugs, 2001, 10, 1819-1830). Several new developments have opened the area for use of nicotinic modulators for therapy of pain (Rowbotham M C et al., Pain, 2009, 146, 245-252). Appropriate modulation of the nicotinic ACh receptors could provide for remedial approach to pain related states.

Another key role of the α7 nAChR is the ability to modulate the production of pro-inflammatory cytokines, like interleukins (IL), tumor necrosis factor alpha (TNF-α), and high mobility group box (HMGB-1) in the central nervous system. Consequently, an anti-inflammatory and antinociceptive effect in pain disorders have been demonstrated (Damaj M I et al., Neuropharmacology, 2000, 39, 2785-2791). Additionally, 'cholinergic anti-inflammatory pathway' is proposed to be a regulatory of local and systemic inflammation and neuro-immune interactions through neural and humoral pathways (Gallowitsch-Puerta M et al., Life Sci., 2007, 80, 2325-2329; Gallowitsch-Puerta and Pavlov 2007; Rosas-Ballina M et al., Mol. Med., 2009, 15, 195-202; Rosas-Ballina M et al., J. Intern. Med., 2009, 265, 663-679). Selective modulators of nicotinic ACh receptors, particularly α7 type, like GTS-21, attenuate cytokine production and IL-1β after endotoxin exposure. Furthermore, α7 nAChR are understood to have a central role in arthritis pathogenesis and potential therapeutic strategy for treatment of joint inflammation (Westman M et al., Scand. J. Immunol., 2009, 70, 136-140). A putative role for α7 nAChR has also been implicated in severe sepsis, endotoxemic shock and systemic inflammation (Jin Y et al. (2010) Int. J. Immunogenet., Liu C et al., Crit. Care. Med., 2009, 37, 634-641).

Angiogenesis, is a critical physiological process for the cell survival and pathologically important for cancer proliferation; several non-neural nicotinic ACh receptors, particularly α7, α5, α3, β2, β4, are involved (Arias H R et al., Int. J. Biochem. Cell. Biol., 2009, 41, 1441-1451; Heeschen C et al., J. Clin. Invest., 2002, 110, 527-536). A role of nicotinic ACh receptors in the development of cervical cancer, lung carcinogenesis and paediatric lung disorders in smoking-exposed population has also been studied (Calleja-Macias I E et al., Int. J. Cancer., 2009, 124, 1090-1096; Schuller H M et al., Eur. J. Pharmacol., 2000, 393, 265-277). Several α7 nAChR agonists, partial agonists, have been characterized for their efficacy in clinical and preclinical studies. EVP-6124, an agonist at α7 nAChR, has demonstrated significant improvement in sensory processing and cognition biomarkers in Phase Ib study with patients suffering from schizophrenia (EnVivo Pharmaceuticals press release 2009, Jan. 12). GTS-21 (DMXB-Anabaseine), an α7 nAChR agonist, in the P II clinical trials, has shown efficacy in improving cognitive deficits in schizophrenia and inhibition of endotoxin-induced TNF-α release (Olincy A et al., Biol. Psychiatry, 2005, 57(8, Suppl.), Abst 44; Olincy A et al., Arch. Gen. Psychiatry, 2006, 63, 630-638; Goldstein R et al., Acad. Emerg. Med., 2007, 14 (15, Suppl. 1), Abst 474). CP-810123, a α7 nAChR agonist, exhibits protection against the scopolamine-induced dementia and inhibition of amphetamine-induced auditory evoked potentials in preclinical studies (O'Donnell C J et al., J. Med. Chem., 2010, 53, 1222-1237). SSR-180711A, also an α7 nAChR agonist, enhances learning and memory, and protects against MK-801/Scopolamine-induced memory loss and prepulse inhibition in preclinical studies (Redrobe J P et al., Eur. J. Pharmacol., 2009, 602, 58-65; Dunlop J et al., J. Pharmacol. Exp. Ther., 2009, 328, 766-776; Pichat P et al., Neuropsychopharmacology, 2007, 32, 17-34). SEN-12333, protected against scopolamine-induced amnesia in passive avoidance test in preclinical studies (Roncarati R et al., J. Pharmacol. Exp. Ther., 2009, 329, 459-468). AR-R-17779, an agonist at α7 nAChR, exhibits improvement in the social recognition task performed in rats (Van K M et al., Psychopharmacology (Berl), 2004, 172, 375-383). ABBF, an agonist at α7 nAChR, improves social recognition memory and working memory in Morris maze task in rats (Boess F G et al., J. Pharmacol. Exp. Ther., 2007, 321, 716-725). TC-5619, a selective α7 nAChR agonist has demonstrated efficacy in animal models of positive and negative symptoms and cognitive dysfunction in schizophrenia (Hauser T A et al., Biochem. Pharmacol., 2009, 78, 803-812).

An alternative strategy to reinforce or potentiate the endogenous cholinergic neurotransmission of ACh without directly stimulating the target receptor is the positive allosteric modulation (PAM) of α7 nAChR (Albuquerque E X et al., Alzheimer Dis. Assoc. Disord., 2001, 15 Suppl 1, S19-S25). Several PAMs have been characterized, albeit in the preclinical stages of discovery. A-86774, α7 nAChR PAM, improves sensory gating in DBA/2 mice by significantly reducing the T:C ratio in a preclinical model of schizophrenia (Faghih R et al., J. Med. Chem., 2009, 52, 3377-3384). XY-4083, an α7 nAChR PAM, normalizes the sensorimotor gating deficits in the DBA/2 mice and memory acquisition in 8-arm radial maze without altering the receptor desensitization kinetics (Ng H J et al., Proc. Natl. Acad. Sci., U.S.A., 2007, 104, 8059-8064). Yet another PAM, PNU-120596, profoundly alters α7 nAChR desensitization kinetics and simultaneously protecting against the disruption of prepulse inhibition by MK-801. NS-1738, another PAM, has exhibited efficacy in-vivo in the animal models of social recognition and spatial memory acquisition in the Morris maze task (Timmermann D B et al., J. Pharmacol. Exp. Ther., 2007, 323, 294-307). In addition, several patents/applications published are listed below—US20060142349, US20070142450, US20090253691, WO2007031440, WO2009115547, WO2009135944, WO2009127678, WO2009127679, WO2009043780, WO2009043784, U.S. Pat. No. 7,683,084, U.S. Pat. No. 7,741,364, WO2009145996, US20100240707, WO2011064288, US20100222398, US20100227869, EP1866314, WO2010130768, WO2011036167, US20100190819 disclose efficacy of allosteric modulators of nicotinic ACh receptors and underscoring their therapeutic potential.

SUMMARY OF THE INVENTION

According to one aspect of the present invention there is provided compounds represented by the general formula I, its tautomeric forms, its stereoisomers, its analogues, its prodrugs, its isotopically substituted analogues, its metabolites, its pharmaceutically acceptable salts, its polymorphs, its solvates, its optical isomers, its clathrates, its co-crystals, their combinations with suitable medicament and pharmaceutical compositions containing them.

Thus the present invention further provides a pharmaceutical composition, containing the compounds of the general formula (I) as defined herein, its tautomeric forms, its stereoisomers, its analogues, its prodrugs, its isotopically substituted analogues, its metabolites, its pharmaceutically acceptable salts, its polymorphs, its solvates, its optical isomers, its clathrates and its co-crystals in combination with the usual pharmaceutically employed carriers, diluents and the like are useful for the treatment and/or prophylaxis of diseases or disorder or condition such as Alzheimer's disease (AD), mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, Huntington's disease, cognitive deficits associated with traumatic brain injury (TBI), cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

The present invention also provides a pharmaceutical composition, containing the compounds of the general formula (I) as defined herein, its tautomeric forms, its stereoisomers, its analogues, its prodrugs, its isotopically substituted analogues, its metabolites, its pharmaceutically acceptable salts, its polymorphs, its solvates, its optical isomers, its clathrates and its co-crystals in combination with the usual pharmaceutically employed carriers, diluents and the like are useful for the treatment and/or prophylaxis of diseases or disorder or condition classified or diagnosed as major or minor neurocognitive disorders, or disorders arising due to neurodegeneration.

The present invention also provides method of administering a compound of formula I, as defined herein in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, traumatic brain injury.

The present invention also provides method of administering a compound of formula I, as defined herein in combination with or as an adjunct to acetylcholinesterase inhibitors, disease modifying drugs or biologics for neurodegenerative disorders, dopaminergic drugs, antidepressants, typical or an atypical antipsychotic.

The present invention also provides use of a compound of formula I as defined herein in the preparation of a medicament for treating a disease or disorder or condition selected from the group classified or diagnosed as major or minor neurocognitive disorders, or disorders arising due to neurodegeneration.

The present invention also provides use of a compound of formula I as defined herein in the preparation of a medicament for treating a disease or disorder or condition selected from the group consisting of attention deficit hyperactivity disorders, schizophrenia, cognitive disorders, Alzheimer's disease, Parkinson's dementia, vascular dementia or dementia associated with Lewy bodies, and traumatic brain injury.

The present invention also provides use of compound of formula I as defined herein in combination with or as an adjunct to acetylcholinesterase inhibitors, disease modifying drugs or biologics for neurodegenerative disorders, dopaminergic drugs, antidepressants, or a typical or atypical antipsychotic.

DETAILED DESCRIPTION OF THE INVENTION

The present invention relates to novel compounds of the general formula I, its tautomeric forms, its stereoisomers, its analogues, its prodrugs, its isotopically substituted analogues, its metabolites, its sulfoxides, its N-oxides, its pharmaceutically acceptable salts, its polymorphs, its solvates, its optical isomers, its clathrates, its co-crystals, their combinations with suitable medicament and pharmaceutical compositions containing them.

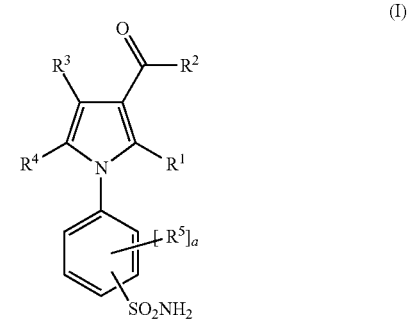

(I)

wherein,
$R^1$ is selected from the group consisting of hydrogen, halogen, substituted- or unsubstituted-alkyl, substituted- or unsubstituted-alkenyl, substituted- or unsubstituted-alkynyl, perhaloalkyl, and substituted- or unsubstituted-cycloalkyl;
$R^2$ is selected from the group consisting of substituted- or unsubstituted-alkyl, $(R^6)(R^7)N-$, $(R^6)N(OR^{7a})-$, and $R^{6a}O-$;
$R^3$ is selected from the group consisting of substituted- or unsubstituted-alkyl, substituted- or unsubstituted-alkenyl, substituted- or unsubstituted-alkynyl, substituted- or unsubstituted-cycloalkyl;
$R^4$ is selected from the group consisting of substituted- or unsubstituted-aryl, substituted- or unsubstituted-heteroaryl;

$[R^5]_a$ is 'a' times repetition of '$R^5$' groups, each $R^5$ is independently selected from the group consisting of halo, substituted- or unsubstituted-alkyl, $R^8O$—; 'a' is an integer selected from 0, 1, and 2;

wherein, $R^6$ and $R^7$ are independently selected from hydrogen, substituted- or unsubstituted-alkyl, $R^9C(=O)$—, $R^9SO_2$—; such that when $R^2$ is $(R^6)(R^7)N$—, $R^6$ and $R^7$ together with the nitrogen atom to which they are attached may form a 3 to 10 member substituted- or unsubstituted-heterocycle containing one to three hetero atoms/groups selected from the group consisting of S, N, O the said heterocycle may be saturated or unsaturated, monocyclic or bicyclic or spiro, or the said heterocycle may contain an alkylene bridge;

$R^{6a}$ is selected from hydrogen and substituted- or unsubstituted-alkyl;

$R^{7a}$ is selected as substituted- or unsubstituted-alkyl;

wherein $R^8$ is selected from hydrogen, substituted- or unsubstituted-alkyl, and perhaloalkyl;

wherein, $R^9$ is independently selected from the group consisting of hydrogen, substituted- or unsubstituted-alkyl, substituted- or unsubstituted-aryl, substituted- or unsubstituted-heteroaryl, substituted- or unsubstituted-cycloalkyl, and substituted- or unsubstituted-heterocyclyl;

wherein, the "alkyl", "alkenyl", and "alkynyl" are substituted with 1 to 6 substituents selected independently from the group consisting of oxo, halogen, nitro, cyano, aryl, hereroaryl, cycloalkyl, $R^{10a}SO_2$—, $R^{10}A^1$-, $R^{10a}C(=O)$—, $R^{10a}C(=O)O$—, $(R^{10})(H)NC(=O)$—, $(R^{10})(alkyl)NC(=O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—;

the "cycloalkyl" is substituted with 1 to 6 substituents selected independently from the group consisting of oxo, halogen, nitro, cyano, aryl, hereroaryl, alkyl, alkenyl, alkynyl, $R^{10a}C(=O)$—, $R^{10a}SO_2$—, $R^{10}A^1$-, $R^{10a}OC(=O)$—, $R^{10a}C(=O)O$—, $(R^{10})(H)NC(=O)$—, $(R^{10})(alkyl)NC(=O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—;

the "aryl" is substituted with 1 to 3 substituents selected independently from the group consisting of halogen, nitro, cyano, hydroxy, $C_1$ to $C_6$ alkyl, $C_2$ to $C_6$ alkenyl, $C_2$ to $C_6$ alkynyl, $C_3$ to $C_6$ cycloalkyl, 3- to 6-membered heterocycle, $C_1$ to $C_6$ perhaloalkyl, alkyl-O—, alkenyl-O—, alkynyl-O—, perhaloalkyl-O—, alkyl-N(alkyl)-, alkyl-N(H)—, $H_2N$—, alkyl-$SO_2$—, perhaloalkyl-$SO_2$—, alkyl-C(=O)N(alkyl)-, alkyl-C(=O)N(H)—, alkyl-N(alkyl)C(=O)—, alkyl-N(H)C(=O)—, $H_2NC(=O)$—, alkyl-N(alkyl)$SO_2$—, alkyl-N(H)$SO_2$—, $H_2NSO_2$—;

the "heterocyclyl" is substituted on ring carbons with 1 to 6 substituents selected independently from the group consisting of oxo, halogen, nitro, cyano, aryl, hereroaryl, alkyl, alkenyl, alkynyl, $R^{10}A^1$-, $R^{10a}OC(=O)$—, $R^{10a}C(=O)O$—, $(R^{10})(H)NC(=O)$—, $(R^{10})(alkyl)NC(O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—;

the "heterocyclyl" is substituted on ring nitrogen(s) with one or more substituents selected from the group consisting of aryl, hereroaryl, alkyl, alkenyl, alkynyl, $R^{10a}C(=O)$—, $R^{10a}SO_2$—, $R^{10a}OC(=O)$—, $(R^{10})(H)NC(=O)$—, $(R^{10})(alkyl)NC(=O)$—;

the "heteroaryl" is substituted with 1 to 3 substituents selected independently from the group consisting of halogen, nitro, cyano, hydroxy, $C_1$ to $C_6$ alkyl, $C_2$ to $C_6$ alkenyl, $C_2$ to $C_6$ alkynyl, $C_3$ to $C_6$ cycloalkyl, 3- to 6-membered heterocycle, $C_1$ to $C_6$ perhaloalkyl, alkyl-O—, alkenyl-O—, alkynyl-O—, perhaloalkyl-O—, alkyl-N(alkyl)-, alkyl-N(H)—, $H_2N$—, alkyl-$SO_2$—, perhaloalkyl-$SO_2$—, alkyl-C(=O)N(alkyl)-, alkyl-C(=O)N(H)—, alkyl-N(alkyl)C(=O)—, alkyl-N(H)C(=O)—, $H_2NC(=O)$—, alkyl-N(alkyl)$SO_2$—, and alkyl-N(H)$SO_2$—, $H_2NSO_2$—;

the "3- to 10-membered heterocyclic ring" is substituted with 1 to 3 substituents selected from the group consisting of oxo, halogen, nitro, cyano, aryl, hereroaryl, alkyl, alkenyl, alkynyl, $R^{10a}C(=O)$—, $R^{10a}SO_2$—, $R^{10}A^1$-, $R^{10a}OC(=O)$—, $R^{10a}C(=O)O$—, $(R^{10})(H)NC(=O)$—, $(R^{10})(alkyl)NC(=O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—;

wherein, $A^1$ is selected from the group consisting of O and S;

$R^{10}$ is selected from hydrogen, alkyl, alkenyl, alkynyl, aryl, heteroaryl, cycloalkyl or heterocyclyl; and $R^{10a}$ is selected from the group consisting of alkyl, alkenyl, alkynyl, perhaloalkyl, aryl, heteroaryl, cycloalkyl or heterocyclyl.

Whenever a range of the number of atoms in a structure is indicated (e.g., a $C_{1-12}$, $C_{1-8}$, $C_{1-6}$, or $C_{1-4}$ alkyl, alkylamino, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, alkylamino, etc.) referenced herein encompasses and specifically describes 1, 2, 3, 4, 5, 6, 7, 8, 9, 10, 11, and/or 12 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 1-9 carbon atoms, 1-10 carbon atoms, 1-11 carbon atoms, 1-12 carbon atoms, 2-3 carbon atoms, 2-4 carbon atoms, 2-5 carbon atoms, 2-6 carbon atoms, 2-7 carbon atoms, 2-8 carbon atoms, 2-9 carbon atoms, 2-10 carbon atoms, 2-11 carbon atoms, 2-12 carbon atoms, 3-4 carbon atoms, 3-5 carbon atoms, 3-6 carbon atoms, 3-7 carbon atoms, 3-8 carbon atoms, 3-9 carbon atoms, 3-10 carbon atoms, 3-11 carbon atoms, 3-12 carbon atoms, 4-5 carbon atoms, 4-6 carbon atoms, 4-7 carbon atoms, 4-8 carbon atoms, 4-9 carbon atoms, 4-10 carbon atoms, 4-11 carbon atoms, and/or 4-12 carbon atoms, etc., as appropriate).

In one of the embodiments of the invention described above, $R^1$ is preferably selected as substituted- or unsubstituted-alkyl.

In any of the embodiments described above, $R^2$ is preferably selected as substituted- or unsubstituted-alkyl.

In any of the embodiments described above, $R^3$ is preferably selected as substituted- or unsubstituted-alkyl.

In any of the embodiments described above, $R^4$ is preferably selected as substituted- or unsubstituted-aryl.

In any of the embodiments described above, 'a' is preferably selected as 0.

In any of the embodiments described above, $R^1$ is preferably selected as substituted- or unsubstituted-alkyl; $R^2$ is preferably selected as substituted- or unsubstituted-alkyl; $R^3$ is preferably selected as substituted- or unsubstituted-alkyl; $R^4$ is preferably selected as substituted- or unsubstituted-aryl; and 'a' is preferably selected as 0.

General terms used in formula can be defined as follows; however, the meaning stated should not be interpreted as limiting the scope of the term per se.

The term "alkyl", as used herein, means a straight chain or branched hydrocarbon containing from 1 to 20 carbon atoms.

Preferably the alkyl chain may contain 1 to 10 carbon atoms. More preferably alkyl chain may contain up to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl.

The term "alkenyl" as used herein, means an 'alkyl' group as defined hereinabove containing 2 to 20 carbon atoms and containing at least one double bond.

The term "alkynyl" as used herein, means an 'alkyl' group as defined hereinabove containing 2 to 20 carbon atoms and containing at least one triple bond.

'Alkyl', 'alkenyl' or 'alkynyl' as defined hereinabove may be substituted with one or more substituents selected independently from the group comprising of oxo, halogen, nitro, cyano, aryl, hereroaryl, cycloalkyl, $R^{10a}SO_2$—, $R^{10}A^1$-, $R^{10a}OC(=O)$—, $R^{10a}C(=O)O$—, $(R^{10})(H)NC(=O)$—, $(R^{10})(alkyl)NC(=O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—; wherein $R^{10}$ is selected from hydrogen, alkyl, alkenyl, alkynyl, aryl, heteroaryl, cycloalkyl or heterocyclyl; and $A^1$ is selected from S and O; and $R^{10a}$ is selected from alkyl, alkenyl, alkynyl perhaloalkyl, aryl, heteroaryl, cycloalkyl or heterocyclyl.

The term "perhaloalkyl" used herein means an alkyl group as defined hereinabove wherein all the hydrogen atoms of the said alkyl group are substituted with halogen. The perhaloalkyl group is exemplified by trifluoromethyl, pentafluoroethyl and the like.

The term "cycloalkyl" as used herein, means a monocyclic, bicyclic, or tricyclic non-aromatic ring system containing from 3 to 14 carbon atoms, preferably monocyclic cycloalkyl ring containing 3 to 6 carbon atoms. Examples of monocyclic ring systems include cyclopropyl, cyclobutyl, cyclopentyl, cyclohexyl, cycloheptyl, and cyclooctyl. Bicyclic ring systems are also exemplified by a bridged monocyclic ring system in which two non-adjacent carbon atoms of the monocyclic ring are linked by an alkylene bridge. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane, bicyclo[3.3.2]decane, bicyclo[3.1.0]hexane, bicyclo[410]heptane, bicyclo[3.2.0]heptanes, octahydro-1H-indene. Tricyclic ring systems are also exemplified by a bicyclic ring system in which two non-adjacent carbon atoms of the bicyclic ring are linked by a bond or an alkylene bridge. Representative examples of tricyclic-ring systems include, but are not limited to, tricyclo[3.3.1.0$^{3.7}$] nonane and tricyclo[3.3.1.1$^{3.7}$]decane (adamantane). The term cycloalkyl also include spiro systems wherein one of the ring is annulated on a single carbon atom such ring systems are exemplified by spiro[2.5]octane, spiro[4.5]decane, spiro[bicyclo[4.1.0]heptane-2,1'-cyclopentane], hexahydro-2'H-spiro[cyclopropane-1,1'-pentalene].

cycloalkyl as defined hereinabove may be substituted with one or more substituents selected independently from the group comprising of oxo, halogen, nitro, cyano, aryl, hereroaryl, alkyl, alkenyl, alkynyl, $R^{10a}C(=O)$—, $R^{10a}SO_2$—, $R^{10}A^1$-, $R^{10a}OC(=O)$—, $R^{10a}C(=O)O$—, $(R^{10})(H)NC(=O)$—, $(R^{10})(alkyl)NC(=O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—; wherein $R^{10}$ is selected from hydrogen, alkyl, alkenyl, alkynyl, aryl, heteroaryl, cycloalkyl or heterocyclyl; and $A^1$ is selected from S and O; and $R^{10a}$ is selected from alkyl, alkenyl, alkynyl, perhaloalkyl, aryl, heteroaryl, cycloalkyl or heterocyclyl The term "aryl" refers to a monovalent monocyclic, bicyclic or tricyclic aromatic hydrocarbon ring system. Examples of aryl groups include phenyl, naphthyl, anthracenyl, fluorenyl, indenyl, azulenyl, and the like. Aryl group also include partially saturated bicyclic and tricyclic aromatic hydrocarbons such as tetrahydro-naphthalene. The said aryl group also includes aryl rings fused with heteroaryl or heterocyclic rings such as 2,3-dihydro-benzo[1,4]dioxin-6-yl; 2,3-dihydrobenzo[1,4]dioxin-5-yl; 2,3-dihydro-benzofuran-5-yl; 2,3-dihydro-benzofuran-4-yl; 2,3-dihydro-benzofuran-6-yl; 2,3-dihydro-benzofuran-6-yl; 2,3-dihydro-1H-indol-5-yl; 2,3-dihydro-1H-indol-4-yl; 2,3-dihydro-1H-indol-6-yl; 2,3-dihydro-1H-indol-7-yl; benzo[1,3]dioxol-4-yl; benzo[1,3]dioxol-5-yl; 1,2,3,4-tetrahydroquinolinyl; 1,2,3,4-tetrahydroisoquinolinyl; 2,3-dihydrobenzothien-4-yl, 2-oxoindolin-5-yl.

Aryl as defined hereinabove may be substituted with one or more substituents selected independently from the group comprising of halogen, nitro, cyano, hydroxy, $C_1$ to $C_6$ alkyl, $C_2$ to $C_6$ alkenyl, $C_2$ to $C_6$ alkynyl, $C_3$ to $C_6$ cycloalkyl, 3- to 6-membered heterocycle, $C_1$ to $C_6$ perhaloalkyl, alkyl-O—, alkenyl-O—, alkynyl-O—, perhaloalkyl-O—, alkyl-N(alkyl)-, alkyl-N(H)—, $H_2N$—, alkyl-$SO_2$—, perhaloalkyl-$SO_2$—, alkyl-C(=O)N(alkyl)-, alkyl-C(=O)N(H)—, alkyl-N(alkyl)C(=O)—, alkyl-N(H)C(=O)—, $H_2NC(=O)$—, alkyl-N(alkyl)$SO_2$—, alkyl-N(H)$SO_2$—, $H_2NSO_2$—.

The term "heteroaryl" refers to a 5-14 membered monocyclic, bicyclic, or tricyclic ring system having 1-4 ring heteroatoms selected from O, N, or S, and the remainder ring atoms being carbon (with appropriate hydrogen atoms unless otherwise indicated), wherein at least one ring in the ring system is aromatic. Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, thienyl, pyrrolyl, oxazolyl, oxadiazolyl, imidazolyl, thiazolyl, isoxazolyl, quinolinyl, pyrazolyl, isothiazolyl, pyridazinyl, pyrimidianyl, pyrazinyl, triazinyl triazolyl, thiadiazolyl, isoquinolinyl, benzoxazolyl, benzofuranyl, indolizinyl, imidazopyridyl, tetrazolyl, benzimidazolyl, benzothiazolyl, benzothiadiazolyl, benzoxadiazolyl, indolyl, azaindolyl, imidazopyridyl, quinazolinyl purinyl, pyrrolo[2,3]pyrimidinyl, pyrazolo[3,4]pyrimidinyl, and benzo(b)thienyl, 2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl and the like.

heteroaryl as defined hereinabove may be substituted with one or more substituents selected independently from the group comprising of halogen, nitro, cyano, hydroxy, $C_1$ to $C_6$ alkyl, $C_2$ to $C_6$ alkenyl, $C_2$ to $C_6$ alkynyl, $C_3$ to $C_6$ cycloalkyl, 3- to 6-membered heterocycle, $C_1$ to $C_6$ perhaloalkyl, alkyl-O—, alkenyl-O—, alkynyl-O—, perhaloalkyl-O—, alkyl-N(alkyl)-, alkyl-N(H)—, $H_2N$—, alkyl-$SO_2$—, perhaloalkyl-$SO_2$—, alkyl-C(=O)N(alkyl)-, alkyl-C(=O)N(H)—, alkyl-N(alkyl)C(=O)—, alkyl-N(H)C(=O)—, $H_2NC(=O)$—, alkyl-N(alkyl)$SO_2$—, and alkyl-N(H)$SO_2$—, $H_2NSO_2$—.

The term "heterocycle" or "heterocyclic" as used herein, means a 'cycloalkyl' group wherein one or more of the carbon atoms replaced by —O—, —S—, —S($O_2$)—, —S(O)—, —N($R'''$)—, —Si($R'''$)$R''$—, wherein, $R'''$ and $R''$ are independently selected from hydrogen, alkyl, alkenyl, alkynyl, aryl, heteroaryl, cycloalkyl, and heterocyclyl. The heterocycle may be connected to the parent molecular moiety through any carbon atom or any nitrogen atom contained within the heterocycle. Representative examples of monocyclic heterocycle include, but are not limited to, azetidinyl, azepanyl, aziridinyl, diazepanyl, 1,3-dioxanyl, 1,3-dioxolanyl, 1,3- dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. Representative examples of bicyclic heterocycle include, but are not limited to 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl and 1,2,3,4-tetrahydroquinolinyl. The term heterocycle also include bridged heterocyclic systems such as azabicyclo[3.2.1]octane, azabicyclo[3.3.1]nonane and the like.

Heterocyclyl group may be substituted on ring carbons with one or more substituents selected independently from the group comprising of oxo, halogen, nitro, cyano, aryl, hereroaryl, alkyl, alkenyl, alkynyl, $R^{10}A^1$-, $R^{10a}OC(=O)$—, $R^{10a}C(=O)O$—, $(R^{10})(H)NC(=O)$—, $(R^{10})(alkyl)NC(O)$—, $R^{10a}C(=O)N(H)$—, $(R^{10})(H)N$—, $(R^{10})(alkyl)N$—, $(R^{10})(H)NC(=A^1)N(H)$—, and $(R^{10})(alkyl)NC(=A^1)N(H)$—; wherein $R^{10}$ is selected from hydrogen, alkyl, alkenyl, alkynyl, aryl, heteroaryl, cycloalkyl or heterocyclyl; and $A^1$ is selected from S and O; and $R^{10a}$ is selected from alkyl, alkenyl, alkynyl, perhaloalkyl, aryl, heteroaryl, cycloalkyl or heterocyclyl.

Heterocyclyl group may further be substituted on ring nitrogen(s) with substituents selected from the group comprising of aryl, hereroaryl, alkyl, alkenyl, alkynyl, $R^{10a}C(=O)$—, $R^{10a}SO_2$—, $R^{10a}OC(=O)$—, $(R^{10})(H)NC(=O)$—, $(R^{10})(alkyl)NC(=O)$—; wherein $R^{10}$ is selected from hydrogen, alkyl, alkenyl, alkynyl, aryl, heteroaryl, cycloalkyl or heterocyclyl; and $R^{10a}$ is selected from alkyl, alkenyl, alkynyl, perhaloalkyl, aryl, heteroaryl, cycloalkyl or heterocyclyl.

The term 'oxo' means a divalent oxygen (=O) attached to the parent group. For example oxo attached to carbon forms a carbonyl, oxo substituted on cyclohexane forms a cyclohexanone, and the like.

The term 'annulated' means the ring system under consideration is either annulated with another ring at a carbon atom of the cyclic system or across a bond of the cyclic system as in the case of fused or spiro ring systems.

The term 'bridged' means the ring system under consideration contain an alkylene bridge having 1 to 4 methylene units joining two non adjacent ring atoms.

A compound its stereoisomers, racemates, pharmaceutically acceptable salt thereof as described hereinabove wherein the compound of general formula I is selected from:
4-(2-(4-chlorophenyl)-3,5-dimethyl-4-propionyl-1H-pyrrol-1-yl)benzenesulfonamide; and
4-(2-(4-chlorophenyl)-3-ethyl-5-methyl-4-propionyl-1H-pyrrol-1-yl)benzenesulfonamide.

Prophetic Compounds are Listed Below:
4-(2-(4-chlorophenyl)-3,5-dimethyl-4-(pyrrolidine-1-carbonyl)-1H-pyrrol-1-yl)benzenesulfonamide.
4-(2-(4-chlorophenyl)-4-((2S,6R)-2,6-dimethylmorpholine-4-carbonyl)-3,5-dimethyl-1H-pyrrol-1-yl)benzenesulfonamide.
4-(3-(3-azabicyclo[3.1.0]hexane-3-carbonyl)-5-(4-chlorophenyl)-2,4-dimethyl-1H-pyrrol-1-yl)benzenesulfonamide.
4-(2-(4-chlorophenyl)-3,5-dimethyl-4-(5-azaspiro[2.5]octane-5-carbonyl)-1H-pyrrol-1-yl)benzenesulfonamide.
4-(3-(8-oxa-3-azabicyclo[3.2.1]octane-3-carbonyl)-5-(4-chlorophenyl)-2,4-dimethyl-1H-pyrrol-1-yl)benzenesulfonamide.

According to another aspect of the present invention, the compounds of general formula I where all the symbols are as defined earlier were prepared by methods described below. However, the invention is not limited to these methods; the compounds may also be prepared by using procedures described for structurally related compounds in the literature.

SCHEME 1

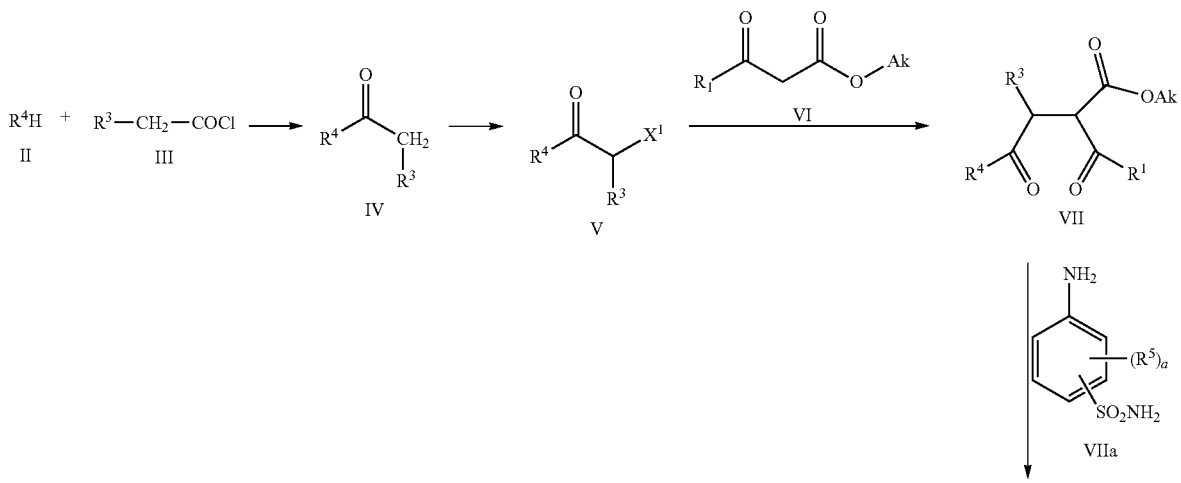

-continued

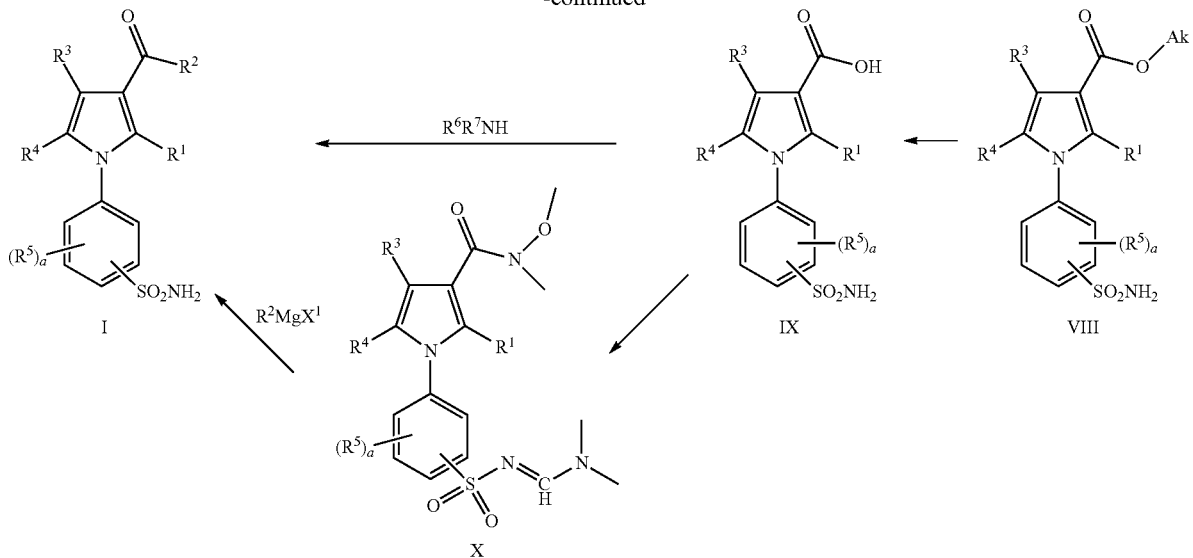

Scheme 1 shows route of synthesis of compound of formula I from compound of formula II.

Compound of formula II is subjected to Friedal-Crafts acylation with acid chloride of formula III in the presence of an acid as described in the literature EP 2168959 to obtain compound of formula IV. Friedal Craft reaction can be carried out under different conditions well known in the art. Besides, a person skilled in the art would appreciate various other possible methods to arrive at compound of formula IV, where $R^3$ and $R^4$ are same as described under compound of formula I hereinabove.

The compounds of the formula IV where $R^3$ and $R^4$ are same as defined earlier in compound of general formula I on halogenation gives compound of formula V. Halogenation can be carried out according to the procedure generally used in the synthetic organic chemistry using bromine, iodine, NCS, NBS, NIS, sufuryl chloride, cupric chloride, cupric bromide or cupric iodide in an organic solvent such as ethyl acetate, dichloromethane, methanol, THF, 1,4-dioxane, or the like, or a suitable mixture thereof. Preferably halogenation is carried out using bromine or cupric chloride in dichloromethane or methanol.

The compound of formula V where symbols $R^3$ and $R^4$ are same as defined for compound IV, and $X^1$ is halogen, when reacted with compound of formula VI, where $R^1$ is same as defined in compound of general formula I, in presence of base such as potassium carbonate, sodium hydride preferably pulverized sodium under room temperature to heated conditions in a solvent such as but not limited to THF, acetonitrile, an aromatic hydrocarbon such as benzene and toluene, preferably toluene provides diketo ester (compound of formula VII).

The compound of the formula VI can be prepared according to the procedure given in literature such as Chem. Pharm. Bull. 1982, 30, 2590 and Journal of Med. Chemistry, 1997, 40, 547.

The compound VII where symbols $R^1$, $R^3$, $R^4$ are same as defined earlier is then reacted with compound of formula VIIa under heating conditions in a solvent such as acetic acid to obtain compound of the formula VIII.

Compound of formula VIIa is generally available commercially or the same can be prepared using procedures provided in literature such as WO200429066 or Chemistry, A European Journal 2011, 17(21), 5903-5907.

Hydrolysis of compound of the formula VIII gives compound of formula IX. The hydrolysis may be carried out by standard procedure generally used in synthetic organic chemistry or well known in the art using reagents such as sodium hydroxide, potassium hydroxide and lithium hydroxide in solvents such as alcohol, THF, water, or their mixture of suitable proportions. Preferably, hydrolysis of compound of formula VIII is carried out using an aqueous solution of sodium hydroxide and ethanol.

The compound of formula IX where $R^1$, $R^3$, $R^4$, $R^5$ and 'a' are same as defined earlier can be converted to its corresponding acid chloride using standard procedures known in synthetic organic chemistry or preferably by reaction with oxalyl chloride in dichloromethane along with DMF followed by reaction with N,O-dimethylhydroxylamine hydrochloride in presence of triethylamine in dichloromethane to provide compounds of formula X.

The compounds of the formula X can be reacted with Grignard reagents $R^2MgX^1$ where $R^2$ is substituted- or unsubstituted-alkyl, and $X^1$ is a halogen, to obtain compound of formula I, where $R^2$ is substituted- or unsubstituted-alkyl. The reaction of compound of formula X with $R^2MgX^1$ may be carried out according to the procedure given in literature such as J. Med. Chem., 2009, 52, 3377.

Compound of formula IX is alternatively reacted with amines of formula $(R^6)(R^7)NH$, $(R^6)(OR^7)NH$, where $R^6$ and $R^7$ are as defined under definition of $R^2$ in general formula I, except $R^9C(=O)$— and $R^9SO_2$—, to obtain compound of formula I, where $R^2$ is selected from $(R^6)(R^7)N$— and $(R^6)(OR^7)N$—, wherein $R^6$ and $R^7$ are as defined under definition of $R^2$ in general formula I, except $R^9C(=O)$— and $R^9SO_2$—. The reaction was carried out according to the conditions known in converting carboxylic acids to amides as known to one skilled in the art. The reaction may be carried out in the presence of solvents, for example, DMF, THF, a halogenated hydrocarbon such as chloroform and dichloromethane, an aromatic hydrocarbon such as xylene, benzene, toluene, or mixtures thereof or the like, in the presence of suitable base such as triethylamine, diisopropylethylamine, pyridine or the like at a temperature between 0-50° C. using reagents such as 1-(3-dimethylaminopropyl)-3-ethylcarbodimide hydrochloride (EDCI), 1,3-dicyclohexylcarbodiimide (DCC), bis(2-oxo-3-oxazolidinyl)phosphinic chloride (BOPCl), O-benzotriazol-1-yl-N,N,N',N'-tetramethyluronium tetrafluoroborate (TBTU), O-(7-aza-benzo triazol-1-yl)-N,N,N',N'-tetramethyluronium hexafluorophosphate (HATU), phosphonium based coupling agents such as 1-benzo-triazolyloxytris-(pyrrolidino) phosphonium hexafluorophosphate (PyBOP), /DMAP, cyclophos, and auxiliary reagents such as 1-hydroxy-7-azabenzotriazole (HOAT), hydroxybenzotriazole hydrate (HOBT) or the like.

The compounds of formula I, wherein $R^2$ is selected as $(R^6)(R^7)N—$ and $(R^6)(OR^{7a})N—$, wherein $R^6$ and $R^7$ are selected from $R^9C(=O)—$ and $R^9SO_2—$, can be prepared using the chemistry described in literature such as Tet. Lett. 2007, 48, 5181-5184 and Syn. Lett. 2005, 13, 2089-2091.

The term 'room temperature' denotes any temperature ranging between about 20° C. to about 40° C., except and otherwise it is specifically mentioned in the specification.

The intermediates and the compounds of the present invention may obtained in pure form in a manner known per se, for example, by distilling off the solvent in vacuum and re-crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography (e.g., flash chromatography) on a suitable support material such as alumina or silica gel using eluent such as dichloromethane, ethyl acetate, hexane, methanol, acetone and their combinations. Preparative LC-MS method is also used for the purification of molecules described herein.

Salts of compound of formula I can be obtained by dissolving the compound in a suitable solvent, for example in a chlorinated hydrocarbon, such as methyl chloride or chloroform or a low molecular weight aliphatic alcohol, for example, ethanol or isopropanol, which was then treated with the desired acid or base as described in Berge S. M. et al. "Pharmaceutical Salts, a review article in Journal of Pharmaceutical sciences volume 66, page 1-19 (1977)" and in handbook of pharmaceutical salts properties, selection, and use by P. H. Einrich Stahland Camille G. wermuth, Wiley-VCH (2002). Lists of suitable salts can also be found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium of salt.

The compound of the invention or a composition thereof can potentially be administered as a pharmaceutically acceptable acid-addition, base neutralized or addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, potassium hydroxide. The conversion to a salt is accomplished by treatment of the base compound with at least a stoichiometric amount of an appropriate acid. Typically, the free base is dissolved in an inert organic solvent such as diethyl ether, ethyl acetate, chloroform, ethanol, methanol, and the like, and the acid is added in a similar solvent. The mixture is maintained at a suitable temperature (e.g., between 0° C. and 50° C.). The resulting salt precipitates spontaneously or can be brought out of solution with a less polar solvent.

The stereoisomers of the compounds of formula I of the present invention may be prepared by stereospecific syntheses or resolution of the achiral compound using an optically active amine, acid or complex forming agent, and separating the diastereomeric salt/complex by fractional crystallization or by column chromatography.

The term "prodrug" denotes a derivative of a compound, which derivative, when administered to warm-blooded animals, e.g. humans, is converted into the compound (drug). The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The prodrugs can be prepared in situ during the isolation and purification of the compounds, or by separately reacting the purified compound with a suitable derivatizing agent. For example, hydroxy groups can be converted into esters via treatment with a carboxylic acid in the presence of a catalyst. Examples of cleavable alcohol prodrug moieties include substituted or unsubstituted, branched or unbranched lower alkyl ester moieties, e.g., ethyl esters, lower alkenyl esters, di-lower alkylamino lower-alkyl esters, e.g., dimethylaminoethyl ester, acylamino lower alkyl esters, acyloxy lower alkyl esters (e.g., pivaloyloxymethyl ester), aryl esters, e.g., phenyl ester, aryl-lower alkyl esters, e.g., benzyl ester, optionally substituted, e.g., with methyl, halo, or methoxy substituents aryl and aryl-lower alkyl esters, amides, lower-alkyl amides, di-lower alkyl amides, and hydroxy amides.

Modulation of the nicotinic cholinergic receptors, particularly α7 may provide for efficacy in a range of cognitive states, right from pre-attention to attention and subsequently working, reference and recognition memory. Accordingly, this invention may find application in the treatment and prophylaxis of multitude of disease conditions including, either one or combinations of, schizophrenia, schizophreniform disorder, cognitive deficits in schizophrenia, brief psychotic disorder, delusional disorder, schizoaffective disorder, shared psychotic disorder, paranoid personality disorder, schizoid personality disorder, schizotypal personality disorder, attention deficit disorder, attention deficit hyperactivity disorder, depression, maniac depression, major depressive disorder, posttraumatic stress disorder, generalized anxiety disorder, tourette's syndrome, cyclothymic disorder, dysthymic disorder, agoraphobia, panic disorder (with or without agoraphobia), phobias (including social phobia) and bipolar disorders (Thomsen M S et al., Curr. Pharm. Des., 2010, 16, 323-343; Peng Z Z et al., Zhonghua Yi Xue Yi Chuan Xue Za Zhi, 2008, 25, 154-158; Young J W et al., Eur. Neuropsychopharmacol., 2007, 17, 145-155; Martin L F et al., Am. J. Med. Genet., B Neuropsychiatr. Genet., 2007, 144B, 611-614; Martin L F et al., Psychopharmacology (Berl), 2004, 174, 54-64; Feher A et al., Dement. Geriatr. Cogn. Disord., 2009, 28, 56-62; Wilens T E et al., Biochem. Pharmacol., 2007, 74, 1212-1223; Verbois S L et al., Neuropharmacology, 2003, 44, 224-233; Sanberg P R et al., Pharmacol. Ther., 1997, 74, 21-25). Cholinergic system, particularly through α7 nAChR seems to have implications in traumatic brain injury-induced psychosis.

Chronic nicotine treatment has shown to attenuate same. Thus, this invention may also find application in the treatment of deficits in cholinergic α7 nAChR following traumatic brain injury (Bennouna M et al., Encephale, 2007, 33, 616-620; Verbois S L et al., Neuropharmacology, 2003, 44, 224-233).

Modulation of nicotinic ACh receptors, particularly the α7 subtype could also help supplement the down-regulated cholinergic receptor expression and transmission as in dementia(s), and also slowing disease progression by reduction of α7-αβ$_{1-42}$ complexation and internalization in AD and Down's syndrome (Nordberg A et al., Neurotox. Res., 2000, 2, 157-165; Haydar S N et al., Bioorg. Med. Chem., 2009, 17, 5247-5258; Deutsch S I et al., Clin. Neuropharmacol., 2003, 26, 277-283). Appropriately, this invention may find application in the treatment and prophylaxis of multitude of disease conditions including, either one or combinations of, dementia(s) due to Alzheimer's disease, dementia with Lewy bodies, Down's syndrome, head trauma, Stroke, hypoperfusion, Parkinson's disease, Huntington's disease, Prion diseases, progressive supranuclear palsy, radiation therapy, brain tumors, normal-pressure hydrocephalus, subdural hematoma, human immunodeficiency virus (HIV) infection, vitamin deficiency, hypothyroidism, drugs, alcohol, lead, mercury, aluminium, heavy metals, syphilis, Lyme disease, viral encephalitis, fungal infection and cryptococcosis (Zhao X et al., Ann. N.Y. Acad. Sci., 2001, 939, 179-186; Perry E et al., Eur. J. Pharmacol., 2000, 393, 215-222; Harrington C R et al., Dementia, 1994, 5, 215-228; Wang J et al., J. Neurosci. Res., 2010, 88, 807-815; Duris K et al., Stroke 2011, 42(12), 3530-6). Thus, this invention may also find application in the prophylaxis and preventive measures immediately after early-stage identification of neurodegenerative disease like Alzheimer's disease and Parkinson's disease.

Modulation of nicotinic ACh receptors particularly α4β2, α3β4 and α7 may have implications in the development of therapies for nicotine, cannabis addiction and relapse prevention. Accordingly, this invention may find application in the prophylaxis or therapy of nicotine addiction, cannabis addiction, and relapse prevention of nicotine or cannabis addiction. Additionally, this invention may also provide for an alternative therapy for non-responding addiction patients, patients having intolerable side-effects with de-addiction therapies or those requiring long-term maintenance therapies. (Kuzmin A et al., Psychopharmacology (Berl), 2009, 203, 99-108; Weiss R B et al., PLoS Genet., 2008, 4, e1000125; Solinas M et al., J. Neurosci., 2007, 27, 5615-5620; Ebbert J O et al., Patient. Prefer. Adherence, 2010, 4, 355-362)

This invention may also find application in the treatment and prophylaxis of multitude of pain conditions including, either one or combinations of, pain arising from, peripheral nervous system (PNS), post-diabetic neuralgia (PDN), post-herpetic neuralgia (PHN), multiple sclerosis, Parkinson's disease, low-back pain, fibromyalgia, post-operative pain, acute pain, chronic pain, mononeuropathy, primary lateral sclerosis, pseudobulbar palsy, progressive muscular palsy, progressive bulbar palsy, postpolio syndrome, diabetes induced polyneuropathy, acute demyelinating polyneuropathy (Guillain-Barre syndrome), acute spinal muscular atrophy (Werdnig-Hoffman disease) and secondary neurodegeneration (Donnelly-Roberts D L et al., J. Pharmacol. Exp. Ther., 1998, 285, 777-786; Rowley T J et al., Br. J. Anaesth., 2010, 105, 201-207; Bruchfeld A et al., J. Intern. Med., 2010, 268, 94-101).

This invention may find application in the treatment and prophylaxis of plethora of inflammation and pain related states involving TNF-α and thus providing symptomatic relief in either any one or combination of, rheumatoid arthritis, bone resorption diseases, atherosclerosis, inflammatory bowel disease, Crohn's disease, inflammation, cancer pain, muscle degeneration, osteoarthritis, osteoporosis, ulcerative colitis, rhinitis, pancreatitis, spondylitis, acute respiratory distress syndrome (ARDS), joint inflammation, anaphylaxis, ischemia reperfusion injury, multiple sclerosis, cerebral malaria, septic shock, tissue rejection of graft, brain trauma, toxic shock syndrome, herpes virus infection (HSV-1 & HSV-2), herpes zoster infection, sepsis, fever, myalgias, asthma, uveititis, contact dermatitis, obesity-related disease and endotoxemia (Giebelen I A T et al., Shock, 2007, 27, 443-447; Pena G et al., Eur. J. Immunol., 2010, 40, 2580-2589).

Thus the present invention further provides a pharmaceutical composition, containing the compounds of the general formula (I) as defined above, its tautomeric forms, its stereoisomers, its analogues, its prodrugs, its isotopically substituted analogues, its metabolites, its pharmaceutically acceptable salts, its polymorphs, its solvates, its optical isomers, its clathrates and its co-crystals in combination with the usual pharmaceutically acceptable carriers, diluents and the like.

The pharmaceutically acceptable carrier (or excipient) is preferably one that is chemically inert to the compound of the invention and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG 400/60% saline), and alcohol (e.g., 40% ethanol/60% water). A preferred pharmaceutical carrier is polyethylene glycol, such as PEG 400, and particularly a composition comprising 40% PEG 400 and 60% water or saline. The choice of carrier will be determined in part by the particular compound chosen, as well as by the particular method used to administer the composition. Accordingly, there is a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting.

The pharmaceutical compositions can be administered parenterally, e.g., intravenously, intraarterially, subcutaneously, intradermally, intrathecally, or intramuscularly. Thus, the invention provides compositions for parenteral administration that comprise a solution of the compound of the invention dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol (for example in topical applications), or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl-β-aminopropionates, and 2-alkyl-imidazoline quaternary ammonium salts, and (e) mixtures thereof.

The parenteral formulations typically will contain from about 0.5% or less to about 25% or more by weight of a compound of the invention in solution. Preservatives and buffers can be used. In order to minimize or eliminate irritation at the site of injection, such compositions can contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well known to those of skill in the art and are suitable in the context of the present invention for application to skin.

Formulations suitable for oral administration can consist of (a) liquid solutions, such as an effective amount of a compound of the invention dissolved in diluents, such as water, saline, or orange juice; (b) capsules, sachets, tablets, lozenges, and troches, each containing a pre-determined amount of the compound of the invention, as solids or granules; (c) powders; (d) suspensions in an appropriate liquid; and (e) suitable emulsions. Liquid formulations can include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the compound ingredient in a flavor, usually sucrose and acacia or tragacanth, as well as pastilles comprising a compound of the invention in an inert base, such as gelatin and glycerin, or sucrose and acacia, emulsions, gels, and the like containing, in addition to the compound of the invention, such excipients as are known in the art.

An compound of the present invention, alone or in combination with other suitable components, can be made into aerosol formulations to be administered via inhalation. A compound or epimer of the invention is preferably supplied in finely divided form along with a surfactant and propellant. Typical percentages of the compounds of the invention can be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute from about 0.1% to about 20% by weight of the composition, preferably from about 0.25% to about 5%. The balance of the composition is ordinarily propellant. A carrier can also be included as desired, e.g., lecithin, for intranasal delivery. These aerosol formulations can be placed into acceptable pressurized propellants, such as dichlorodifluoromethane, propane, nitrogen, and the like. They also can be formulated as pharmaceuticals for non-pressured preparations, such as in a nebulizer or an atomizer. Such spray formulations can be used to spray mucosa.

Additionally, the compound of the invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the compound ingredient, such carriers as are known in the art to be appropriate.

The concentration of the compound in the pharmaceutical formulations can vary, e.g., from less than about 1% to about 10%, to as much as 20% to 50% or more by weight, and can be selected primarily by fluid volumes, and viscosities, in accordance with the particular mode of administration selected.

For example, a typical pharmaceutical composition for intravenous infusion could be made up to contain 250 ml of sterile Ringer's solution, and 100 mg of at least one compound of the invention. Actual methods for preparing parenterally administrable compounds of the invention will be known or apparent to those skilled in the art and are described in more detail in, for example, *Remington's Pharmaceutical Science* ($17^{th}$ ed., Mack Publishing Company, Easton, Pa., 1985).

It will be appreciated by one of ordinary skill in the art that, in addition to the aforedescribed pharmaceutical compositions, the compound of the invention can be formulated as inclusion complexes, such as cyclodextrin inclusion complexes, or liposomes. Liposomes can serve to target a compound of the invention to a particular tissue, such as lymphoid tissue or cancerous hepatic cells. Liposomes can also be used to increase the half-life of a compound of the invention. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837, 028, and 5,019,369.

The compounds or pharmaceutical compositions are useful, in an embodiment, for the treatment and/or prophylaxis of diseases or disorder or condition such as Alzheimer's disease (AD), mild cognitive impairment (MCI), senile dementia, vascular dementia, dementia of Parkinson's disease, attention deficit disorder, attention deficit hyperactivity disorder (ADHD), dementia associated with Lewy bodies, AIDS dementia complex (ADC), Pick's disease, dementia associated with Down's syndrome, Huntington's disease, cognitive deficits associated with traumatic brain injury (TBI), cognitive decline associated with stroke, poststroke neuroprotection, cognitive and sensorimotor gating deficits associated with schizophrenia, cognitive deficits associated with bipolar disorder, cognitive impairments associated with depression, acute pain, post-surgical or post-operative pain, chronic pain, inflammation, inflammatory pain, neuropathic pain, smoking cessation, need for new blood vessel growth associated with wound healing, need for new blood vessel growth associated with vascularization of skin grafts, and lack of circulation, arthritis, rheumatoid arthritis, psoriasis, Crohn's disease, ulcerative colitis, pouchitis, inflammatory bowel disease, celiac disease, periodontitis, sarcoidosis, pancreatitis, organ transplant rejection, acute immune disease associated with organ transplantation, chronic immune disease associated with organ transplantation, septic shock, toxic shock syndrome, sepsis syndrome, depression, and rheumatoid spondylitis.

In another embodiment, the pharmaceutical compositions are useful for the treatment and/or prophylaxis of diseases or disorder or condition classified or diagnosed as major or minor neurocognitive disorders, or disorders arising due to neurodegeneration.

The present invention also provide method of administering a compound of formula I, as defined hereinabove in combination with or as adjunct to medications used in the treatment of attention deficit hyperactivity disorders, schizophrenia, and other cognitive disorders such as Alzheimer's disease, Parkinson's dementia, vascular dementia or dementia associated with Lewy bodies, traumatic brain injury.

The present invention also provide method of administering a compound of formula I, as defined hereinabove in combination with or as an adjunct to acetylcholinesterase inhibitors, disease modifying drugs or biologics for neurodegenerative disorders, dopaminergic drugs, antidepressants, typical or an atypical antipsychotic.

Accordingly, compound of formula I is useful for preventing or treating a disorder mediated by nicotinic acetylcholine receptors. Such compounds can be administered to a subject having such a disorder or susceptible to such disorders in a therapeutically effective amount. The compounds are particularly useful for a method of treating a mammal having a condition where modulation of nicotinic acetylcholine receptor activity is of therapeutic benefit, wherein the method is accomplished by administering a therapeutically effective amount of a compound of formula I to a subject having, or susceptible to, such a disorder. The present invention also provides a pharmaceutical composition, containing the compounds of the general formula (I) as defined above, its tautomeric forms, its stereoisomers, its analogs, its prodrugs, its isotopes, its metabolites, its pharmaceutically acceptable salts, its polymorphs, its solvates, its optical isomers, its clathrates and its co-crystals in combination with the usual pharmaceutically employed carriers, diluents and the like, and for use in any of the methods described herein.

The compounds of the invention can be administered in a dose sufficient to treat the disease, condition or disorder. Such doses are known in the art (see, for example, the *Physicians' Desk Reference* (2004)). The compounds can be administered using techniques such as those described in, for example, Wasserman et al., *Cancer*, 36, pp. 1258-1268 (1975) and *Physicians' Desk Reference*, 58th ed., Thomson PDR (2004).

Suitable doses and dosage regimens can be determined by conventional range-finding techniques known to those of ordinary skill in the art. Generally, treatment is initiated with smaller dosages that are less than the optimum dose of the compound of the present invention. Thereafter, the dosage is increased by small increments until the optimum effect under the circumstances is reached. The present method can involve the administration of about 0.1 μg to about 50 mg of at least one compound of the invention per kg body weight of the individual. For a 70 kg patient, dosages of from about 10 μg to about 200 mg of the compound of the invention would be more commonly used, depending on a patient's physiological response.

By way of example and not intending to limit the invention, the dose of the pharmaceutically active agent(s) described herein for methods of treating or preventing a disease or condition as described above can be about 0.001 to about 1 mg/kg body weight of the subject per day, for example, about 0.001 mg, 0.002 mg, 0.005 mg, 0.010 mg, 0.015 mg, 0.020 mg, 0.025 mg, 0.050 mg, 0.075 mg, 0.1 mg, 0.15 mg, 0.2 mg, 0.25 mg, 0.5 mg, 0.75 mg, or 1 mg/kg body weight per day. The dose of the pharmaceutically active agent(s) described herein for the described methods can be about 1 to about 1000 mg/kg body weight of the subject being treated per day, for example, about 1 mg, 2 mg, 5 mg, 10 mg, 15 mg, 0.020 mg, 25 mg, 50 mg, 75 mg, 100 mg, 150 mg, 200 mg, 250 mg, 500 mg, 750 mg, or 1000 mg/kg body weight per day.

In accordance with embodiments, the present invention provides methods of treating, preventing, ameliorating, and/or inhibiting a condition modulated by the nicotinic acetylcholine receptor comprising administering a compound of formula (I) or a salt thereof.

The terms "treat," "prevent," "ameliorate," and "inhibit," as well as words stemming therefrom, as used herein, do not necessarily imply 100% or complete treatment, prevention, amelioration, or inhibition. Rather, there are varying degrees of treatment, prevention, amelioration, and inhibition of which one of ordinary skill in the art recognizes as having a potential benefit or therapeutic effect. In this respect, the inventive methods can provide any amount of any level of treatment, prevention, amelioration, or inhibition of the disorder in a mammal. For example, a disorder, including symptoms or conditions thereof, may be reduced by, for example, 100%, 90%, 80%, 70%, 60%, 50%, 40%, 30%, 20%, or 10%. Furthermore, the treatment, prevention, amelioration, or inhibition provided by the inventive method can include treatment, prevention, amelioration, or inhibition of one or more conditions or symptoms of the disorder, e.g., cancer. Also, for purposes herein, "treatment," "prevention," "amelioration," or "inhibition" can encompass delaying the onset of the disorder, or a symptom or condition thereof.

In accordance with the invention, the term subject includes an "animal" which in turn includes a mammal such as, without limitation, the order Rodentia, such as mice, and the order Lagomorpha, such as rabbits. It is preferred that the mammals are from the order Carnivora, including Felines (cats) and Canines (dogs). It is more preferred that the mammals are from the order Artiodactyla, including Bovines (cows) and Swine (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

Following are the abbreviations used and meaning thereof in the specification:
ACh: Acetylcholine.
AD: Alzheimer's disease.
ADC: AIDS dementia complex.
ADHD: attention deficit hyperactivity disorder.
AIDS: Acquired immunodeficiency syndrome.
ARDS: acute respiratory distress syndrome.
DCC: 1,3-dicyclohexylcarbodiimide.
DCE: dichloroethane.
DCM: dichloromethane.
DIPEA: diisopropyl ethyl amine
DLB: dementia with Lewy bodies.
DMF: N,N-dimethylformamide.
EDCI: 1-(3-dimethylaminopropyl)-3-ethylcarbodimide hydrochloride.
FLIPR: Fluorometric Imaging Plate Reader.
HATU: 2-(1H-7-Azabenzotriazol-1-yl)-1,1,3,3-tetramethyl uronium hexafluorophosphate.
HBSS: Hank's balanced salt solution.
HEPES: 4-(2-hydroxyethyl)piperazine-1-ethanesulfonic acid.
HMGB: high mobility group box.
HOAT: 1-hydroxy-7-azabenzotriazole.
HOBT: hydroxybenzotriazole hydrate.
HPLC: High Performance liquid chromatography.
IL: interleukins.
LDT: laterodorsal tegmental nucleus.
LGIC: ligand-gated ion channels.
MCI: mild cognitive impairment.
NBS: N-bromosuccinimide.
NCS: N-chlorosuccinimide.
NIS: N-iodosuccinimide
NNRs: Neural nicotinic ACh receptors.
PAM: positive allosteric modulation.
PD: Parkinson's disease.
PDN: post-diabetic neuralgia.
PHN: post-herpetic neuralgia.
PMBO: p-methoxy benzyloxy.
PNS: peripheral nervous system.
TBI: traumatic brain injury.
THF: Tetrahydrofuran.
TLC: Thin layer chromatography.
TMS: tetramethylsilane.
TNF-α: tumor necrosis factor alpha.
VTA: ventral tegmental area.
α7 nAChR: nicotinic acetylcholine receptor α7 subunit.

The following examples are provided to further illustrate the present invention and therefore should not be construed in any way to limit the scope of the present invention. All $^1$HNMR spectra were determined in the solvents indicated and chemical shifts are reported in δ units downfield from the internal standard tetramethylsilane (TMS) and interproton coupling constants are reported in Hertz (Hz).

EXAMPLE 1

Synthesis of 4-(2-(4-chlorophenyl)-3,5-dimethyl-4-propionyl-1H-pyrrol-1-yl)benzenesulfonamide (Compound 1)

Step 1: Ethyl 5-(4-chlorophenyl)-2,4-dimethyl-1-(4-sulfamoylphenyl)-1H-pyrrole-3-carboxylate

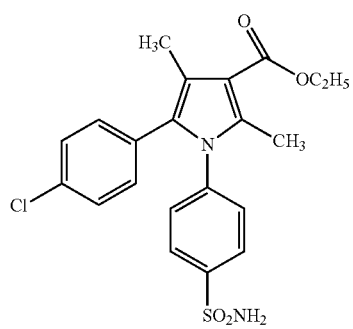 [SMILES: CCOC(=O)c1c(C)c(-c2ccc(Cl)cc2)n(-c2ccc(S(N)(=O)=O)cc2)c1C]

A mixture of ethyl[2-acetyl-4-(4-chlorophenyl)-3-methyl-4-oxo]butyrate (prepared according to the procedure given in Med. Chem. Res. (1994), 5, 54-62, 1.6 g, 5.39 mmol) and 4-aminobenzenesulfonamide (0.928 g, 5.39 mmol) in acetic acid (40 ml) was heated at 95° C. for 17 hr under stirring. The completion of reaction was monitored by TLC. Reaction mixture was concentrated at reduced pressure. Dichloromethane (100 ml) was added to the residue, washed with water (1×25 ml). Organic layer was dried over anhydrous $Na_2SO_4$. The solvent was evaporated under reduced pressure to obtain a crude product; which was purified by column chromatography over silica gel (100-200 mesh) using 1% methanol in dichloromethane as an eluent to yield the title compound (1.65 g, 71%)

MS: m/z 433 (M+1)
$^1$HNMR ($CDCl_3$, 400 MHz): δ 7.90 (d, J=8.4 Hz, 2H), 7.16-7.25 (m, 4H), 6.92 (d, J=8.4 Hz, 2H), 4.93 (bs, exchanged with $D_2O$ 2H), 4.33 (q, J=7.2 Hz, 2H), 2.37 (s, 3H), 2.23 (s, 3H), 1.38 (t, J=7.2 Hz, 3H).

Step 2: 5-(4-Chlorophenyl)-2,4-dimethyl-1-(4-sulfamoylphenyl)-1H-pyrrole-3-carboxylic acid

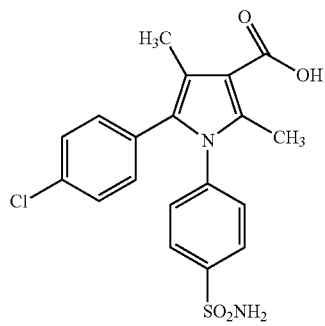 [SMILES: Cc1c(C(=O)O)c(C)n(-c2ccc(S(N)(=O)=O)cc2)c1-c1ccc(Cl)cc1]

Ethyl 5-(4-chlorophenyl)-2,4-dimethyl-1-(4-sulfamoylphenyl)-1H-pyrrole-3-carboxylate (Step 1, 1.6 g, 3.69 mmol) was suspended in ethanol (50 ml) and treated with aqueous solution of NaOH (2.22 g in 20 ml. water) at room temperature. The reaction mixture was refluxed for 3 hr. The completion of reaction was monitored by TLC. Reaction mixture was concentrated at reduced pressure. Residue was taken in mixture of solvents ethyl acetate and dichloromethane in 1:1 ratio (75 ml.). Organic layer was decanted and solid so obtained was taken in water (25 ml) and neutralized with 5N HCl upto pH7, Aqueous layer was extracted with ethyl acetate (2×50 ml). Combined organic layer was dried over anhydrous $Na_2SO_4$. The solvent was evaporated under reduced pressure to obtain a product. (1.47 g, 98%)

MS: m/z 405 (M+1)
$^1$HNMR (DMSO-D6, 400 MHz): δ 12.03 (bs, exchanges with $D_2O$, 1H), 7.80 (d, J=8.4 Hz, 2H), 7.41 (bs, exchanged with $D_2O$ 2H), 7.38 (d, J=8.4 Hz, 2H), 7.31 (d, J=8.4 Hz, 2H), 7.06 (d, J=8.4 Hz, 2H), 2.28 (s, 3H), 2.15 (s, 3H).

Step 3: 5-(4-Chlorophenyl)-1-(4-(N-((dimethylamino)methylene) sulfamoyl)phenyl)-N-methoxy-N,2,4-trimethyl-1H-pyrrole-3-carboxamide

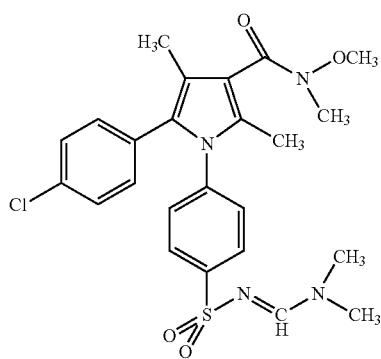 [SMILES: CON(C)C(=O)c1c(C)c(-c2ccc(Cl)cc2)n(-c2ccc(S(=O)(=O)/N=C/N(C)C)cc2)c1C]

Oxalyl chloride (0.908 g, 0.60 ml, 7.16 mmol) was added dropwise at 0° C. to a solution of 5-(4-Chlorophenyl)-2,4-dimethyl-1-(4-sulfamoylphenyl)-1H-pyrrole-3-carboxylic acid (step 2, 1.45 g, 3.58 mmol) in dichloromethane (50 ml)/DMF (0.544 g, 0.50 ml, 7.16 m mol). Mixture was allowed to come at room temperature and stirred for 1 hr. under nitrogen atmosphere. The completion of reaction was monitored by TLC. The mixture was concentrated under reduced pressure under nitrogen atmosphere. To this residue was added N,O-dimethylhydroxylamine hydrochloride (0.690 g, 7.16 mmol) in dry dichloromethane (50 ml) at 0° C. followed by the addition of triethylamine (1.44 g, 2.0 ml, 14.32 mmol,) under stirring. The reaction mixture was stirred at room temperature for 2 hr. The completion of reaction was monitored by TLC. The solvent was removed under reduced pressure. The residue so obtained was taken in dichloromethane (50 ml), washed with water (2×25 ml.) and organic layers separated were dried over anhydrous sodium sulphate, filtered and concentrated at reduced pressure to get a crude product. This crude product was purified by column chromatography over silica gel (100-200 mesh) using 0.8% methanol in dichloromethane as an eluent to yield the title compound (0.763 g, 42%).

MS: m/z 503 (M+1)
$^1$HNMR (CDCl$_3$, 400 MHz): δ 8.13 (s, 1H), 7.82 (d, J=8.4 Hz, 2H), 7.15 (d, J=8.4 Hz, 2H), 7.10 (d, J=8.4 Hz, 2H), 6.91 (d, J=8.4 Hz, 2H), 3.67 (s, 3H), 3.37 (s, 3H), 3.15 (s, 3H), 3.04 (s, 3H), 2.13 (s, 3H), 2.10 (s, 3H).

Step 4: 4-(2-(4-chlorophenyl)-3,5-dimethyl-4-propionyl-1H-pyrrol-1-yl)benzenesulfonamide

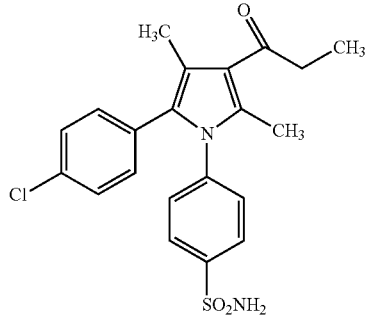 [SMILES: CCC(=O)c1c(C)c(-c2ccc(Cl)cc2)n(-c2ccc(S(N)(=O)=O)cc2)c1C]

To a stirred solution of 5-(4-Chlorophenyl)-1-(4-(N-((dimethylamino)methylene) sulfamoyl)phenyl)-N-methoxy-N,2,4-trimethyl-1H-pyrrole-3-carboxamide (step 3, 0.750 g, 1.49 mmol) in anhydrous THF (50 ml) at 0° C., ethyl magnesium bromide (Grignard reagent, 0.994 g, 7.4 ml, 7.46 mmol) was added dropwise and reaction mixture was heated to reflux for 1 h. The completion of reaction was monitored by TLC. After cooling, reaction mixture was quenched by addition of solution of saturated ammonium chloride (10 ml) and extracted with ethyl acetate (1×50 ml). Combined organic layer was dried over anhydrous $Na_2SO_4$. The solvent was evaporated under reduced pressure to obtain a crude product; which was purified by column chromatography over silica gel (100-200 mesh) using 0.4% methanol in dichloromethane as an eluent to yield the title compound which was finally purified by preparative HPLC (0.062 g, 10%)

MS: m/z 417 (M+1)
$^1$HNMR (CDCl$_3$, 400 MHz): δ 7.88 (d, J=8.8 Hz, 2H), 7.16-7.19 (m, 4H), 6.91 (d, J=8.4 Hz, 2H), 4.92 (bs, exchanged with $D_2O$ 2H), 2.84 (q, J=7.2 Hz, 2H), 2.34 (s, 3H), 2.24 (s, 3H), 1.21 (t, J=7.2 Hz, 3H).

EXAMPLE 2

Preparation of 4-(2-(4-chlorophenyl)-3-ethyl-5-methyl-4-propionyl-1H-pyrrol-1-yl)benzenesulfonamide (Compound 2)

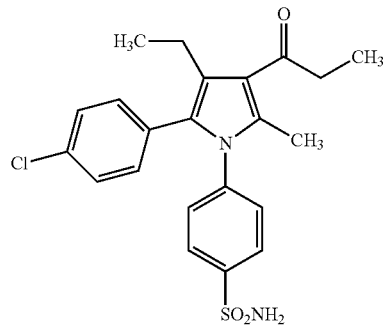 [SMILES: CCC(=O)c1c(CC)c(-c2ccc(Cl)cc2)n(-c2ccc(S(N)(=O)=O)cc2)c1C]

Compound 2 was prepared using appropriate reagents and by following a procedure analogous to the one provided under example 1.

4-(2-(4-chlorophenyl)-3-ethyl-5-methyl-4-propionyl-1H-pyrrol-1-yl)benzenesulfonamide (Compound 2)

MS: m/z 431 (M+1),
$^1$HNMR (DMSO-D6, 400 MHz): δ 7.78 (d, J=8.4 Hz, 2H), 7.46 (bs-exchanged with D$_2$O, 2H), 7.39 (d, J=8.4 Hz, 2H), 7.31 (d, J=8.4 Hz, 2H), 7.10 (d, J=8.4 Hz, 2H), 2.82 (q, J=7.2 Hz, 2H), 2.53 (q, J=7.2 Hz, 2H), 2.26 (s, 3H), 1.10 (t, J=7.2 Hz, 3H), 1.02 (t, J=7.2 Hz, 3H).

EXAMPLE 3

Pharmacological Screening

Compounds were tested in a cell-based real-time kinetic assay in human IMR-32 cells with native expression of α7nAChR. The increase in intracellular Ca$^{2+}$ levels was measured in a Fluorometric Imaging Plate Reader (FLIPR). Test compound and agonist solutions were made in assay buffer (HBSS, pH 7.4, 20 mM HEPES, and 10 mM CaCl$_2$). Briefly, cells were plated into Poly-D-Lysine coated back-walled clear-bottom 96-well microplates at a density of 80,000 to 100,000 cells/well and incubated at 37° C./5% CO$_2$ for 40-48 h prior to the experiment. For evaluation of compound mediated potentiation of agonist response, growth media was removed from the wells and 200 μl of FLIPR calcium 4 dye (Molecular Devices), reconstituted in assay buffer, and was added to the wells. After dye loading, microplates were incubated for 30 min at 37° C. and 30 min at room temperature and then directly transferred to the FLIPR. Baseline fluorescence was monitored for the first 10 to 30 s followed by the addition of 25 μl of test compound solution and subsequent monitoring of fluorescence changes for up to 10 min. This was followed by addition of 25 μl of agonist solution (PNU-282987, 10 μM) and measurement of fluorescence for 4 min. (Faghih R. et al. 2009, J. Med. Chem., 52, 3377-84.)

The compound induced fold increase in agonist response (fold PAM activity) was computed by dividing the maximum effect (Max-Min fluorescence) obtained with test compound in presence of agonist with the agonist-alone effect. EC$_{50}$ of the compound was calculated using GraphPad Prism software version 5.0, by plotting compound concentrations against fold PAM activity.

Fold activity at 1 μM concentration: Compounds of invention showed increase in the activity by between about 20 to about 25 folds.

The invention claimed is:
1. A compound of formula I, its tautomeric forms, its stereoisomers, or its pharmaceutically acceptable salts,

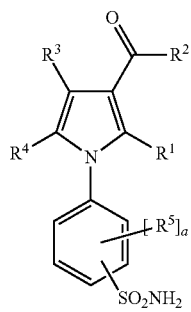

(I)

wherein,
R$^1$ is selected from the group consisting of hydrogen, halogen, substituted- or unsubstituted- C$_1$-C$_4$ alkyl, and C$_1$-C$_4$ perhaloalkyl;
R$^2$ is selected from the group consisting of substituted- or unsubstituted- C$_1$-C$_4$ alkyl, (R$^6$)(R$^7$)N—, (R$^6$)N(OR$^{7a}$)—, and R$^{6a}$O—;
R$^3$ is substituted- or unsubstituted-C$_1$-C$_4$ alkyl;
R$^4$ is selected from the group consisting of phenyl or phenyl substituted with halogen, nitro, cyano, hydroxy, C$_1$-C$_4$ alkyl, C$_1$-C$_4$ alkyl-O, C$_1$-C$_4$ perhaloalkyl, H$_2$N—, and H$_2$NC(=O)—;
[R$^5$]$_a$ is 'a' times repetition of 'R$^5$' groups, each R$^5$ is independently selected from the group consisting of halo C$_1$-C$_4$ alkyl, and R$^8$O—; 'a' is an integer selected from 0, 1, and 2;
wherein, R$^6$ and R$^7$ are independently selected from hydrogen, C$_1$-C$_4$ alkyl; such that when R$^2$ is (R$^6$)(R$^7$)N—, R$^6$ and R$^7$ together with the nitrogen atom to which they are attached may form a 3 to 10 member substituted- or unsubstituted-heterocycle containing one to three hetero atoms/groups selected from the group consisting of S, N, O the said heterocycle may be saturated or unsaturated, monocyclic or bicyclic or spiro, or the said heterocycle may contain an alkylene bridge;
R$^{6a}$ is selected from hydrogen and C$_1$-C$_4$ alkyl;
R$^{7a}$ is C$_1$-C$_4$ alkyl;
wherein R$^8$ is selected from hydrogen, C$_1$-C$_4$ alkyl, and C$_1$-C$_4$ perhaloalkyl;
wherein,
the "substituted C$_1$-C$_4$ alkyl" is substituted with 1 to 4 substituents selected independently from the group consisting of oxo, halogen, nitro, cyano, R$^{10a}$SO$_2$—, R$^{10}$A$^1$-, R$^{10a}$OC(=O)—, R$^{10a}$C(=O)O—, (R$^{10}$)(H)NC(=O)—, (R$^{10}$)(C$_1$-C$_4$ alkyl)NC(=O)—, R$^{10a}$C(=O)N(H)—, (R$^{10}$)(H)N—, (R$^{10}$)(C$_1$-C$_4$ alkyl)N—, (R$^{10}$)(H)NC(=A$^1$)N(H)—, and (R$^{10}$)(C$_1$-C$_4$ alkyl)NC(=A$^1$)N(H)—;
the "substituted 3- to 10-membered heterocyclic ring" is substituted with 1 to 3 substituents selected from the group consisting of oxo, halogen, nitro, cyano, C$_1$-C$_4$ alkyl, R$^{10a}$C(=O)—, R$^{10a}$SO$_2$—, R$^{10}$A$^1$-, R$^{10a}$OC(=O)—, R$^{10a}$C(=O)O—, (R$^{10}$)(H)NC(=O)—, (R$^{10}$)(C$_1$-C$_4$ alkyl)NC(=O)—, R$^{10a}$C(=O)N(H)—, (R$^{10}$)(H)N—, (R$^{10}$)(C$_1$-C$_4$ alkyl)N—, (R$^{10}$)(H)NC(=A$^1$)N(H)—, and (R$^{10}$)(C$_1$-C$_4$ alkyl)NC(=A$^1$)N(H)—;
wherein,
A$^1$ is selected from the group consisting of O and S;
R$^{10}$ is selected from hydrogen and C$_1$-C$_4$ alkyl; and
R$^{10a}$ is selected from the group consisting of C$_1$-C$_4$ alkyl and C$_1$-C$_4$ perhaloalkyl.

2. The compound of formula I, its tautomeric forms, its stereoisomers or its pharmaceutically acceptable salts as claimed in claim 1, wherein R$^1$ is selected as substituted- or unsubstituted-C$_1$-C$_4$ alkyl.

3. The compound of formula I, its tautomeric forms, its stereoisomers or its pharmaceutically acceptable salts, as claimed in claim 1, wherein R$^2$ is selected as substituted- or unsubstituted-C$_1$-C$_4$ alkyl.

4. The compound of formula I, its tautomeric forms, its stereoisomers, or its pharmaceutically acceptable salts as claimed in claim 1, wherein 'a' is selected as 0.

5. The compound of formula I, its tautomeric forms, its stereoisomers as claimed in claim 1, wherein R$^1$ is selected as substituted- or unsubstituted-C$_1$-C$_4$ alkyl; R$^2$ is selected as substituted- or unsubstituted-C$_1$-C$_4$ alkyl; R$^3$ is selected as substituted- or unsubstituted-$C_1$-$C_4$ alkyl; $R^4$ is selected as phenyl substituted with halogen; and 'a' is selected as 0.

6. The compound of formula I, its tautomeric forms, its stereoisomers, or its pharmaceutically acceptable salts as claimed in claim 1, wherein the compound of formula I is selected from—
- 4-(2-(4-chlorophenyl)-3,5-dimethyl-4-propionyl-1H-pyrrol-1-yl) benzenesulfonamide; and
- 4-(2-(4-chlorophenyl)-3-ethyl-5-methyl-4-propionyl-1H-pyrrol-1-yl)benzenesulfonamide.

7. A pharmaceutical composition comprising a compound of claim 1 and a pharmaceutically acceptable carrier.

\* \* \* \* \*

UNITED STATES PATENT AND TRADEMARK OFFICE
CERTIFICATE OF CORRECTION

PATENT NO. : 9,187,420 B2
APPLICATION NO. : 14/007458
DATED : November 17, 2015
INVENTOR(S) : Neelima Sinha et al.

Page 1 of 1

It is certified that error appears in the above-identified patent and that said Letters Patent is hereby corrected as shown below:

IN THE CLAIMS

Column 28, Line 65, Claim 5, delete "stereoisomers" and insert -- stereoisomers, or its pharmaceutically acceptable salts --

Signed and Sealed this
Twenty-ninth Day of March, 2016

Michelle K. Lee
*Director of the United States Patent and Trademark Office*